(12) United States Patent
Koziara et al.

(10) Patent No.: US 10,039,718 B2
(45) Date of Patent: Aug. 7, 2018

(54) USE OF SOLID CARRIER PARTICLES TO IMPROVE THE PROCESSABILITY OF A PHARMACEUTICAL AGENT

(75) Inventors: Joanna M. Koziara, Foster City, CA (US); Mark M. Menning, Foster City, CA (US); Robert G. Strickley, Foster City, CA (US); Richard Yu, Foster City, CA (US); Brian P. Kearney, Foster City, CA (US); Anita A. Mathias, Foster City, CA (US)

(73) Assignee: Gilead Sciences, Inc., Foster City, CA (US)

( * ) Notice: Subject to any disclaimer, the term of this patent is extended or adjusted under 35 U.S.C. 154(b) by 1252 days.

(21) Appl. No.: 12/434,513

(22) Filed: May 1, 2009

(65) Prior Publication Data

US 2009/0324729 A1 Dec. 31, 2009

Related U.S. Application Data

(60) Provisional application No. 61/049,935, filed on May 2, 2008, provisional application No. 61/150,655, filed on Feb. 6, 2009, provisional application No. 61/150,652, filed on Feb. 6, 2009.

(51) Int. Cl.

| | |
|---|---|
| A61K 31/535 | (2006.01) |
| A61K 9/20 | (2006.01) |
| A61K 9/16 | (2006.01) |
| A61K 9/48 | (2006.01) |
| A61K 31/00 | (2006.01) |
| A61K 31/5377 | (2006.01) |

(52) U.S. Cl.
CPC .......... *A61K 9/2086* (2013.01); *A61K 9/1611* (2013.01); *A61K 9/2009* (2013.01); *A61K 9/2054* (2013.01); *A61K 9/2077* (2013.01); *A61K 9/4866* (2013.01); *A61K 31/00* (2013.01); *A61K 31/5377* (2013.01)

(58) Field of Classification Search
CPC .................................................. C07D 405/12
USPC ..................................................... 514/231.5
See application file for complete search history.

(56) References Cited

U.S. PATENT DOCUMENTS

| | | |
|---|---|---|
| 3,400,197 A | 9/1968 | Lippmann et al. |
| 4,254,099 A | 3/1981 | Asmussen et al. |
| 4,603,143 A | 7/1986 | Schmidt |
| 5,559,158 A * | 9/1996 | Al-Razzak ............. A61K 9/143 424/451 |
| 5,591,451 A | 1/1997 | Gupta et al. |
| 5,597,926 A | 1/1997 | Kempf et al. |
| 5,696,270 A | 12/1997 | Kempf et al. |
| 5,888,548 A | 3/1999 | Wongsuragrai et al. |
| 5,922,695 A | 7/1999 | Arimilli et al. |
| 5,948,438 A | 9/1999 | Staniforth et al. |
| 6,030,645 A | 2/2000 | Tritsch et al. |
| 6,342,249 B1 | 1/2002 | Wong et al. |
| 6,524,615 B2 | 2/2003 | Gutierrez-Rocca et al. |
| 6,531,610 B1 | 3/2003 | Kempf et al. |
| 6,960,251 B2 | 11/2005 | Uhrlandt et al. |
| 7,026,507 B2 | 4/2006 | Heyl-Frank et al. |
| 7,176,220 B2 | 2/2007 | Satoh et al. |
| 7,217,431 B2 | 5/2007 | Holm et al. |
| 7,749,537 B2 | 7/2010 | Hite et al. |
| 8,148,374 B2 | 4/2012 | Desai et al. |
| 2002/0015715 A1 | 2/2002 | Beaurline et al. |
| 2002/0091159 A1 | 7/2002 | Spireas |
| 2002/0127274 A1 | 9/2002 | Kushla et al. |
| 2002/0197311 A1 | 12/2002 | Hasenzahl et al. |
| 2003/0004182 A1 | 1/2003 | Gierer |
| 2003/0035834 A1 | 2/2003 | Seth |
| 2003/0068368 A1 | 4/2003 | Kushla et al. |
| 2003/0158263 A1 | 8/2003 | Radhakrishnan et al. |
| 2004/0022844 A1 | 2/2004 | Hasenzahl et al. |
| 2004/0022848 A1 | 2/2004 | Kikuchi et al. |
| 2004/0057992 A1 | 3/2004 | Gierer |

(Continued)

FOREIGN PATENT DOCUMENTS

| | | |
|---|---|---|
| AU | 34967/89 | 11/1989 |
| CN | 1582169 A | 2/2005 |

(Continued)

OTHER PUBLICATIONS

Evonik: AEROPERL product data sheet. Accessed at http://www.aerosil.com/product/aerosil/en/products/granulated-products/pages/default.aspx on Nov. 13, 2011.*

(Continued)

*Primary Examiner* — Raymond J Henley, III

(74) *Attorney, Agent, or Firm* — Fish & Richardson P.C.

(57) ABSTRACT

The invention provides a composition comprising, a compound of formula (I):

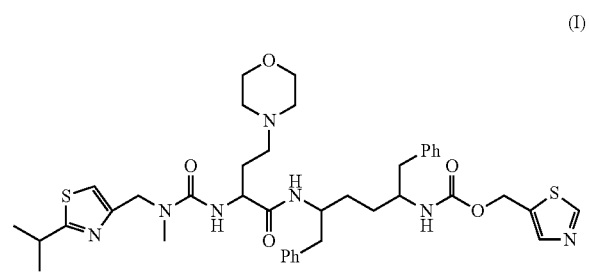

(I)

or a pharmaceutically acceptable salt thereof and a plurality of solid carrier particles, as well as methods for using the composition to inhibit the activity of cytochrome P-450.

26 Claims, 6 Drawing Sheets

(56) References Cited

U.S. PATENT DOCUMENTS

| | | |
|---|---|---|
| 2004/0101555 A1 | 5/2004 | Clouatre et al. |
| 2004/0254210 A1 | 12/2004 | Haeberlin et al. |
| 2005/0084529 A1 | 4/2005 | Rosenberg et al. |
| 2005/0095287 A1 | 5/2005 | Matharu et al. |
| 2005/0096390 A1 | 5/2005 | Holm et al. |
| 2005/0096391 A1 | 5/2005 | Holm et al. |
| 2005/0106244 A1 | 5/2005 | Kushla et al. |
| 2005/0238675 A1 | 10/2005 | Li et al. |
| 2005/0239819 A1 | 10/2005 | Satoh et al. |
| 2006/0068015 A1 | 3/2006 | Holm et al. |
| 2006/0093667 A1 | 5/2006 | Gierer |
| 2006/0105050 A1 | 5/2006 | Holm et al. |
| 2006/0110444 A1 | 5/2006 | Holm et al. |
| 2006/0115524 A1 | 6/2006 | Eliasen |
| 2006/0182691 A1 | 8/2006 | Besse et al. |
| 2006/0229210 A1 | 10/2006 | Neugebauer et al. |
| 2006/0292192 A1 | 12/2006 | Hasenzahl et al. |
| 2007/0009603 A1 | 1/2007 | Holm et al. |
| 2007/0014846 A1 | 1/2007 | Holm et al. |
| 2007/0014854 A1 | 1/2007 | Zalit et al. |
| 2007/0026062 A1 | 2/2007 | Holm et al. |
| 2007/0110800 A1 | 5/2007 | Gierer |
| 2007/0122482 A1 | 5/2007 | Holm et al. |
| 2007/0196504 A1 | 8/2007 | Kikuchi et al. |
| 2007/0298108 A1 | 12/2007 | Svete et al. |
| 2008/0207620 A1 | 8/2008 | Desai et al. |
| 2010/0016448 A1 | 1/2010 | Kothari et al. |
| 2010/0215753 A1 | 8/2010 | Sherwood et al. |
| 2010/0285122 A1 | 11/2010 | Oliyai et al. |
| 2010/0285157 A1 | 11/2010 | Hirai et al. |
| 2014/0017199 A1 | 1/2014 | Desai et al. |
| 2014/0343062 A1 | 11/2014 | Kearney et al. |
| 2014/0343063 A1 | 11/2014 | Kearney et al. |
| 2015/0150810 A1 | 6/2015 | Oliyai et al. |

FOREIGN PATENT DOCUMENTS

| | | |
|---|---|---|
| EP | 0163178 | 12/1985 |
| EP | 0345109 | 12/1989 |
| EP | 0486948 | 5/1992 |
| EP | 0727419 A2 | 8/1996 |
| EP | 0783889 | 7/1997 |
| EP | 0867177 | 9/1998 |
| EP | 0997459 A1 | 5/2000 |
| EP | 1004296 | 5/2000 |
| EP | 1241134 | 9/2002 |
| EP | 1287823 | 3/2003 |
| EP | 1800681 | 6/2007 |
| EP | 2393485 | 12/2011 |
| EP | 1564210 | 8/2015 |
| FR | 2767071 | 2/1999 |
| GB | 1241024 | 7/1971 |
| GB | 1317400 | 5/1973 |
| GB | 1422974 | 1/1976 |
| JP | 2761374 B2 | 6/1998 |
| JP | 3569240 B2 | 9/2004 |
| JP | 2005-2092 | 1/2005 |
| JP | 2005-075826 | 3/2005 |
| JP | 2005-508977 A | 4/2005 |
| JP | 2007-39338 | 2/2007 |
| JP | 4018664 | 12/2007 |
| JP | 2008-543861 | 12/2008 |
| KR | 10-0255897 | 6/1992 |
| KR | 10/2008/0091767 | 10/2008 |
| WO | WO 1992/20669 | 11/1992 |
| WO | WO 1994/14436 | 7/1994 |
| WO | WO-94/28902 A1 | 12/1994 |
| WO | WO-97/03675 A1 | 2/1997 |
| WO | WO 2002/087546 | 11/2002 |
| WO | WO 2003/004001 | 1/2003 |
| WO | WO 2003/030868 | 4/2003 |
| WO | WO 2003/037379 | 5/2003 |
| WO | WO-2003/037379 A1 | 5/2003 |
| WO | WO 2003/047551 | 6/2003 |
| WO | WO 2004/064845 | 8/2004 |
| WO | WO 2004/073687 | 9/2004 |
| WO | WO 2004/073689 | 9/2004 |
| WO | WO 2005/087199 | 9/2005 |
| WO | WO-2005/113508 A1 | 12/2005 |
| WO | WO 2006/000229 | 1/2006 |
| WO | WO-2006/135932 A2 | 12/2006 |
| WO | WO-2006/135932 A3 | 12/2006 |
| WO | WO 2006/135933 | 12/2006 |
| WO | WO 2007/068934 | 6/2007 |
| WO | WO 2007/074472 | 7/2007 |
| WO | WO 2007/076874 | 7/2007 |
| WO | WO 2007/097333 | 8/2007 |
| WO | WO 2007/111866 | 10/2007 |
| WO | WO 2008/010921 | 1/2008 |
| WO | WO 2008/017867 | 2/2008 |
| WO | WO 2008/029417 | 3/2008 |
| WO | WO 2008/103949 | 8/2008 |
| WO | WO-2009/037449 A1 | 3/2009 |
| WO | WO-2009/135179 A2 | 11/2009 |
| WO | WO-2009/135179 A3 | 11/2009 |
| WO | WO 2010/091197 | 8/2010 |
| WO | WO 2010/115886 | 10/2010 |
| WO | WO 2017/132158 | 8/2017 |

OTHER PUBLICATIONS

Rowe, R.C. et al., Ed. Handbook of Pharmaceutical Excipients 5E (2006): entry for alcohol (ethanol), pp. 18-20.*

CAS entry for ritonavir. Accessed at http://scifinder.cas.org on Aug. 15, 2012.*

Search Report and Written Opinion of the International Searching Authority, PCT/US2009/042607, dated Apr. 4, 2011, 10 pages.

J.M. Huber Corporation, "Product Dossier, Synethetic Amorphous Silica", Huber Engineered Materials, www.hubermaterials.com, pp. 1-14, 2010.

Degussa, "Product Information, AEROPERL® 300 Pharma, Collodal Silicon Dioxide", www.aerosil.com, 2 pages, 2006.

Evonik Industries, "Specification, AEROPERL® 300 Pharma", ZJQ_SPEZ/DEG/Jun. 17, 2010/16:32/p04aas25/001, JQP0001, 2 pages, 2010.

J.M. Huber Corporation, "North America Silica Specifications, Zeofree®5161 Product Specifications", Huber Engineered Materials, 1 page, 2009.

Blachez, P., et al., "Development of Tablets with Self-Micro-Emulsifying Drug Delivery System (SMEDDS)", AAPS Annual Meeting and Exposition Abstract, W 5114, 2005.

Goncalves, E., et al., "Solid Microemulsions Prepared by Adsorption of Microemulsion Preconcentrates onto Silicas", AAPS Annual Meeting and Exposition, Abstract, T3112, 2006.

Bauer et al., "Ritonavir: An Extraordinary Example of Conformational Polymorphism", *Pharmaceutical Research*, vol. 18, No. 6, 859-866 (2001).

Law et al., "Physicochemical Considerations in the Preparation of Amorphous Ritonavir—Poly(ethylene glycol) 8000 Solid Dispersions", *Journal of Pharmaceutical Sciences*, vol. 90, No. 8, 1015-1025 (2001).

NORVIR® label revision approved on Nov. 20, 2012, NDA No. 022417, Reference ID 3219583, 44 pages.

European Medicines Agency (EMEA) (2007). ATRIPLA Monograph, Scientific Discussion, forty-eight total pages.

German, P. et al. (Nov. 1, 2010). "Pharmacokinetics and Bioavailability of an Integrase and Novel Pharmacoenhancer-Containing Single-Tablet Fixed-Dose Combination Regimen for the Treatment of HIV," *J. Acquired Immune Deficiency Syndromes* 55(3):323-329.

Gunsel et al. (1989). "Chapter 5: Compression-Coated and Layer Tablets," in *Pharmaceutical Dosage Forms: Tablets*, Lieberman et al., eds., vol. 1, 2nd Edition, pp. 274-284.

Hammer, S. et al. (Aug. 6, 2008). "Antiretroviral Treatment of Adult HIV Infection. 2008 Recommendations of the International AIDS Society: USA Panel," *JAMA* 300(5):555-570.

Martinez-Cajas, J.L. et al. (2008). "Antiretroviral Therapy: Optimal Sequencing of Therapy to Avoid Resistance," *Drugs* 68(1):43-72.

Phillips, A.N. et al. (Dec. 8, 2007). "Risk of Extensive Virological Failure to the Three Original Antiretroviral Drug Classes Over

(56) References Cited

OTHER PUBLICATIONS

Long-Term Follow-up from the Start of Therapy in Patients with HIV Infection: An Observational Cohort Study," *Lancet* 370(9603):1923-1928.
Szczech, L.A. (Jan. 1, 2008). "Tenofovir Nephrotoxicity: Focusing Research Questions and Putting Them into Clinical Context," *J. Infectious Diseases* 197(1):7-9.
Von Wyl, V.V. et al. (2007). "Emergence of HIV-1 Drug Resistance in Previously Untreated Patients Initiating Combination Antiretroviral Treatment," *Archives of Internal Medicine* 167(16):1782-1790.
African Regional mailed on Mar. 6, 2014 for African Regional Patent Application No. APP2010005429, filed on May 1, 2009, three pages.
African Regional mailed on Mar. 6, 2014 for African Regional Patent Application No. APP2011005857, filed on Feb. 4, 2010, eight pages.
Canadian Office Action dated Feb. 27, 2014 for Canadian Patent Application No. 2,720,856, filed on May 1, 2009, one page.
Chinese Office Action dated Jul. 24, 2014, for Chinese Patent Application No. 200980115840.X, filed on May 1, 2009, nine pages.
Columbian Office Action dated Apr. 11, 2014, for Columbian Patent Application No. 10134187A, filed on Apr. 5, 2013, ten pages.
Eurasian Office Action dated Feb. 20, 2014, for Eurasian Patent Application No. 201071173, filed on May 1, 2009, two pages.
European Communication dated Apr. 3, 2013, for European Patent Application No. 09739981.0, filed on May 1, 2009, four pages.
European Communication dated Oct. 30, 2013, for European Patent Application No. 09739981.0, filed on May 1, 2009, eight pages.
European Communication dated Jun. 16, 2014, for European Patent Application No. 09739981.0, filed on May 1, 2009, four pages.
European Communication dated Oct. 10, 2011, for European Patent Application 10 703 766.5, filed on Feb. 4, 2010, two pages.
International Search Report dated Apr. 8, 2011, for PCT Application No. PCT/US2010/023226, filed on Feb. 4, 2010, five pages.
Israeli Office Action dated Jul. 13, 2014, for Israeli Patent Application No. 214227, filed on Feb. 4, 2010, two pages.
Israeli Office Action dated Jun. 29, 2014, for Israeli Patent Application No. 208614, filed on May 1, 2009, two pages.
Japanese Office Action dated Jan. 28, 2014 for Japanese Patent Application No. 2011-549268, filed on Feb. 4, 2010, five pages.
Japanese Office Action dated Jun. 9, 2014, for Japanese Patent Application No. 2011-507697, filed on May 1, 2009, five pages.
Mexican Office Action dated Apr. 15, 2014 for Mexican Patent Application No. Mx/a/2011/008289, filed on Feb. 4, 2010, eleven pages.
Peruvian Office Action dated May 6, 2014, for Peruvian Patent Application No. 1449, filed on Feb. 4, 2010, twelve pages.
Written Opinion of the International Searching Authority dated Apr. 8, 2011, for PCT Application No. PCT/US2010/023226, filed on Feb. 4, 2010, seven pages.
Chinese Office Action dated Sep. 28, 2014, for Chinese Patent Application No. 201310447258.1, filed on Sep. 27, 2013, twelve pages.
Brown, K.C. et al. (2009). "Drug Interactions with News and Investigational Antiretrovirals," *Clin. Pharmacokinet.* 48(4):211-241.
Final Office Action dated Nov. 7, 2014, for U.S. Appl. No. 12/700,608, filed Feb. 4, 2010, twenty-three pages.
Bolivian Office Action dated Dec. 9, 2014 for Bolivian Patent Application No. SP00292010, filed on Feb. 5, 2010, 6 pages.
Chilean Office Action dated Dec. 17, 2014, for Chilean Application No. 1885-2011, filed on Feb. 4, 2010, 10 pages.
Chilean Office Action dated Sep. 8, 2015, for Chilean Application No. 1885-2011 filed on Feb. 4, 2010, twenty pages.
Chinese Office Action dated Aug. 13, 2015, for Chinese Patent Application No. 201310447258.1 filed on Sep. 27, 2013, eight pages.
Chinese Office Action dated Feb. 24, 2016, for Chinese Patent Application No. 201310447258.1 filed on Sep. 27, 2013, twelve pages.
Indonesian Office Action dated May 26, 2015, for Indonesian Patent Application No. W00201004105 filed on May 1, 2009, two pages.
Indian Examination Report dated Mar. 11, 2016, for Indian Application No. 7565/DELNP/2010 filed on Oct. 27, 2010, three pages.
Korean Office Action dated Sep. 23, 2015, for Korean Patent Application No. 10-2011-7020652 filed on Feb. 4, 2010, four pages.
Japanese Notice of Allowance dated Mar. 10, 2016, for Japanese Patent Application No. 2014-178005 filed on Feb. 4, 2010, six pages.
"ATRIPLA" (last updated Mar. 2016) Evidence of EMA Scientific Discussion Publication (1 page).
"ATRIPLA", (Jul. 2006), Product Label (50 pages).
"Emtriva", (Nov. 2011), Prescribing information, Gilead Sciences, (29 pages).
"Truvada", (Nov. 2008), Product Label, Gilead Sciences, (34 pages).
"Viread", (Jan. 2012), Prescribing information, Gilead Sciences, (48 pages).
AEROPERL®, (Feb. 10, 2008), "Special Granulated Fumed Silicas", (web archive), www.aerosil.com, (1 page).
African Office Action in African Application No. AP/P/2010/005429, dated Apr. 11, 2013, 8 pages.
Allen et al., (2005), "Ansel's Pharmaceutical Dosage Forms and Drug Delivery Systems", Eighth Edition, (pp. 227-229), ©Lippincott Williams & Wilkins, (5 pages).
Allen et al., (2005), "Ansel's Pharmaceutical Dosage Forms and Drug Delivery Systems", Eighth Edition, (pp. 42 and 43), ©Lippincott Williams & Wilkins, (4 pages).
Applicant's Letter in European Application No. 10703766.5-1219, dated Apr. 20, 2012, 4 pages.
Ash et al., (2007), "Handbook of Fillers, Extenders and Diluents", Second Edition, (Extract), Synapse Information Resources, Inc., (3 pages).
Aulton, M.E., (2002), "Pharmaceutics, The Science of Dosage Form Design", (Chapter 8), Second Edition, ©Elsevier Limited, (28 pages).
Australian Office Examination report dated Apr. 30, 2013, for Australian Patent Application No. 2009242451, 3 pages.
Australian Office Examination report dated Nov. 17, 2015, for Australian Patent Application No. 2015200637, filed on Feb. 4, 2010, two pages.
Becker, S. L., (2003), "The Role of Pharmacological Enhancement in Protease Inhibitor-Based Highly Active Antiretroviral Therapy", Expert Opin. Investig. Drugs, 12(3):401-412.
Chayan et al., "Porous Silicon: an Effective Nucleation-inducing Material for Protein Crystallization," JMB, 2001, 312:591-595.
Chinese Office Action in Chinese Application No. 200980115840.X, dated Dec. 13, 2012, 18 pages (with English translation).
Chinese Office Action in Chinese Application No. 200980115840.X, dated Mar. 19, 2012, 7 pages (with English translation).
Chinese Office Action in Chinese Application No. 201080006646.0, dated Jan. 31, 2013, 6 pages (with English translation).
Chinese Office Action in Chinese Application No. 201080006646.0, dated Jul. 9, 2012, 10 pages (with English translation).
Coffey, S. MD., (2009), "New Pharmacokinetic Booster on the Horizon", HIV Meds Quarterly Research Brief, (1 page).
Collins, S., (Apr. 4, 2007), "Phase 2 Study of Gileads Integrase Inhibitor Elvitegravir (GS-9137)", HIV Treatment Bulletin, (3 pages).
Colombian Office Action in Colombian Application No. 10-134.187, dated Dec. 4, 2012, 12 pages (English translation only).
Colombian Office Action in Colombian Application No. 10-134.187, dated Feb. 4, 2011, 3 pages (English translation only).
Colombian Office Action in Colombian Application No. 10-134.187, dated Mar. 19, 2013, 12 pages (English translation only).
Columbian Office Action dated Dec. 23, 2015, for Columbian Patent Application No. 11114720, filed on Feb. 4, 2010, 10 pages.

(56) References Cited

OTHER PUBLICATIONS

Endale et al., (Mar. 1, 2008), "Granulation of Roller Compaction and Enteric Coated Tablet Formulation of the D13 Extract of the Seeds of Glinus Lotoides Loaded on Aeroper® 300 Pharma", AAPS PharmSciTech, 9(1):31-38.
Eurasian Office Action in Eurasian Application No. 201071173, dated Aug. 23, 2012, 6 pages. (with English translation).
Eurasian Office Action in Eurasian Application No. 201491658, dated Nov. 10, 2016, 4 pages (with English translation).
Eurasian Office Action in Eurasian Application No. 201591353, dated Jan. 17, 2017, 6 pages (with English translation).
Eurasian Office Action dated May 5, 2015, for Eurasian Patent Application No. 201491658, filed on Feb. 4, 2010, four pages.
European Communication Notice and Annex to the Notice of Opposition against European Patent No. 2296633B1, dated Jun. 29, 2016 for European Patent Application No. 09739981.0, filed on May 1, 2009, 29 pages.
European Communication, Notice and Annex to the Notice of Opposition against European Patent No. 2393485B1, dated Apr. 22, 2016 for European Patent Application 10703766.5, filed on Feb. 4, 2010, 15 pages.
European Communication, Notice and Statement of Opposition, dated Jun. 30, 2016, for European Patent Application No. 09739981.0, filed on May 1, 2009, 14 pages.
European Communication, Response to Notices of Opposition against European Patent No. 2296633B1, filed Dec. 16, 2016, 24 pages.
European Medicines Agency (EMEA) (2005). "Norvir," Scientific Discussion, 19 pages.
European Medicines Agency Assessment Report on Stibild®, (Mar. 21, 2013), (147 pages).
European Medicines Agency Assessment Report on Tybost®, (Jul. 25, 2013), (86 pages).
European Search Report in European Application No. 15184628.4, dated Jan. 18, 2016, 11 pages.
Evonik Industries, "AEROPERL® 300/30," Product Information, Feb. 2016, 2 pages.
Evonik Industries, "Aerosil, Colloidal Silicon Dioxide for Pharmaceuticals," Technical Information TI-1281, Oct. 2008, 24 pages.
Exhibit D25, "Photographs of cobicistat before and after formulation," in Response to Notices of Opposition against European Patent No. 2296633B1, filed Dec. 16, 2016, 1 page.
Exhibit D26, Technical Annex, "Experimental report," in Response to Notices of Opposition against European Patent No. 2296633B1, filed Dec. 16, 2016, 2 pages.
Extract from the Register of European Patents in European Patent No. EP2393485, accessed May 19, 2016, 3 pages.
Handbook of Pharmaceutical Excipients, Fourth Edition, Ed. R.d C. Rowe, P. J. Sheskey and P.J. Weller, published 2003: pp. 185-188.
Gilead Sciences, (Jan. 27, 2009), "Gilead Outlines R&D Priorities for 2009", Gilead Press Release, (3 pages).
Gilead Sciences, (Jul. 22, 2008), "Gilead Initiates Phase III Clinical Trial of Elvitegravir, an Investigational Integrase Inhibitor for HIV", Gilead Press Release, (2 pages).
Indonesian Office Action dated Jan. 8, 2016, for Indonesian Patent Application No. WO0201103098, filed on Feb. 4, 2010, two pages.
Israeli Office Action dated Oct. 29, 2015, for Israeli Patent Application No. 214227, filed on Feb. 4, 2010, three pages.
Japanese Office Action dated Jul. 28, 2015, for Japanese Patent Application No. 5911927, filed on Feb. 4, 2010, five pages.
Korean Office Action in Korean Application No. 10-2016-7020504, dated Sep. 13, 2016, 3 pages (English translation only).
Korean Office Action in Korean Application No. 10-2016-7025826, dated Dec. 29, 2016, 8 pages (with English translation).
Korean Office Action dated Mar. 22, 2016, for Korean Patent Application No. 10-2010-026980, filed on May 9, 2009, four pages.
Lachman, L., (1986), "Preformulation", Theory and Practice of Industrial Pharmacy, chapter 8, (7 pages).

Mathias, A.A. et al., (Oct. 1, 2007), "Bioequivalence of Efavirenz/Emtricitabine/Tenofovir Disoproxil Fumarate Single-Tablet Regimen", J Acquir Immune Defic Syndr, 46(2):167-173.
Mexican Office Action dated Apr. 14, 2016 for Mexican Patent Application No. Mx/a/2014/015438, filed on Oct. 29, 2010, nine pages.
New Zealand Office Action in New Zealand Application No. 588978, dated Apr. 12, 2011, 2 pages.
New Zealand Office Action in New Zealand Application No. 588978, dated Nov. 29, 2012, 1 page.
New Zealand Office Action in New Zealand Application No. 588978, dated Oct. 26, 2012, 1 page.
Non-Final Office Action dated Aug. 5, 2016, for U.S. Appl. No. 14/616,563, filed Feb. 6, 2015, 22 pages.
Pakistan Office Action in Pakistan Application No. 94/2010, dated Aug. 2010, 3 pages (English translation only).
Ramanathan, S. et al., (Jul. 1, 2007), "Pharmacokinetics of Emtricitabine, Tenofovir, and GS-9137 Following Coadministration of Emtricitabine/Tenofovir Disoproxil Fumarate and Ritonavir-Boosted GS-9137", J Acquir Immune Defic Syndr, 45(3):274-279, (7 pages).
Rowe, R.C. et al., (2003), "Handbook of Pharmaceutical Excipients", (Fourth Edition), Pharmaceutical Press, pp. 108-111; 181-183; 289-293; and 354-357, (18 pages).
Shimara, K. et al., (2008), "Elvitegravir: An Emerging HIV Integrase Inhibitor", Drug Evaluation, Future HIV Ther.,2(5):411-418.
T 0484/09 Data Sheet for the Decision of Sep. 18, 2014, (25 pages).
T 0512/02 Data Sheet for the Decision of Oct. 26, 2006, (14 pages).
Ukrainian Office Action in Ukrainian Application No. a2011-10569, dated Oct. 30, 2012, 4 pages (with English translation).
Vietnamese Office Action in Vietnamese Application No. 1-2011-02035, dated Oct. 29, 2013, 4 pages (with English translation).
WHO Model List of Essential Medicines, (Mar. 2007), (36 pages).
Written Opinion of the International Searching Authority dated Apr. 4, 2011, for PCT Patent Application No. PCT/US2009/042607, filed on May 1, 2009, six pages.
Opponents, Teva Pharmaceutical Industries Ltd., Statement of Grounds of Appeal, filed Apr. 23, 2018 in European Opposition of European Patent No. 2296633, 24 pages.
Opponents, Richard Cooke, Statement of Grounds of Appeal, filed Apr. 22, 2018 in European Opposition of European Patent No. 2296633, 11 pages.
Gore et al., "Surface Chemistry of Colloidal Silica and a Possible Application to Stabilize Aspirin in Solid Matrixes," J. Pharm. Sci. 68 (1979), pp. 197-202.
Avbunudiogba et al., "Effect of Humidity on the Physical Properties of Aspirin Tablets Produced by Melt Granulation and Slugging Methods," Journal of Pharmacy and Biological Sciences, 5 (2013), 20-25.
Notice of Appeal, Opposition to European Patent No. 2296633, Teva Pharmaceutical Industries Ltd, Filed Feb. 9, 2018, 1 page.
Notice of Appeal, Gilead Science, Inc., European Patent No. 2296633, filed Feb. 20, 2018, 2 pages.
Notice of Appeal, Opposition to European Patent No. 229663, Richard Cooke, Filed Feb. 20, 2018, 1 page.
Aerosil® and Aeroperl® Colloidal Silicon Dioxide for Pharmaceuticals, technical Information TI 1281, twenty-four pages.
Annex 1, Summary of Product Characteristics, filed on Sep. 27, 2017, in opposition in European Patent No. 2296633B1, twenty-one pages.
Annex to the communication, dated Mar. 2, 2017, in opposition in European Patent No. 2296633B1, eleven pages.
Annexure C in Indian Pre-Grant Opposition in Indian Application No. 7565/DELNP/2010, dated Jan. 28, 2013, 1 page.
Chinese Office Action in Chinese Application No. 2015104083760, dated Jun. 2, 2017, 30 pages (with English translation).
Chinese Office Action in Chinese Application No. 20151048376.0, dated Jun. 2, 2017, (with English translation) thirty-one pages.
Ecuadoran Office Action in Ecuadoran Application No. SP-10-10636, dated Jun. 28, 2017, 14 pages.

(56) References Cited

OTHER PUBLICATIONS

Endale et al., "Standardisation and physicochemical characterisation of the extracts of seeds of Glinus lotoides,"Pharmazie 59: 34-38 (2004), five pages.
Eurasian Office Action in Eurasian Application No. 201591353, dated Jul. 26, 2017, 11 pages (with English translation).
Examination Report in Australian Application No. 2016250470, dated Aug. 8, 2017, 6 pages.
Indian Pre-Grant Opposition in Indian Application No. 7565/DELNP/2010, dated Jan. 30, 2013, 18 pages.
Information about the result of oral proceedings in European Patent No. 2296633B1, dated Oct. 30, 2017, one page.
Isolation, Structural Elucidation, Quantification and Formulation of the Saponins and Flavonoids of the Seeds of Gunus Lotoides, Dissertation of Abebe Endale Mengesha, dated Aug. 29, 2005, thirty pages.
Japanese Office Action in Japanese PTE Application No. 2017-700004, dated Jun. 6, 2017 (with English translation) six pages.
Japanese Office Action in Japanese PTE Application No. 2017-700005, dated Jun. 6, 2017 (with English translation) seven pages.
Opponents Further Submission, filed Aug. 30, 2017, in opposition in European Patent No. 2296633B1, six pages.
Patentee's letter regarding the opposition procedure dated Oct. 23, 2017, in opposition in European Patent No. 2296633B1, one page.
Patentee's Submissions under Rule 116 EPC, filed Aug. 30, 2017, in opposition in European Patent No. 2296633B1, two pages.
Preliminary Opinion in European Application No. 097399810, dated Mar. 2, 2017, 18 pages.
Request for postponement of oral proceedings in European Patent No. 2296633B1, dated Mar. 17, 2017, two pages.
Sipernat® 50, Product Information, Jul. 2017, two pages.
Summons to attend oral proceedings pursuant to Rule 115(1) EPC, issued in European Patent No. 2296633B1, dated Mar. 2, 2017, one page.
Vietnamese Office Action in Vietnamese Application No. 1-2011-02929, dated Jun. 7, 2017 (with English translation) four pages.
Patentee's Statement of Grounds of Appeal and Auxiliary Requests, Opposition of European Patent No. 229633B1, Filed Apr. 20, 2018, 16 pages.
"Aeroperl 300 Pharma—a versatile carrier for liquid or low-solubility APIs—Aerosil Fumed silica," Retrieved from the Internet: http://www.aerosil.com/product/en/industries/pharmaceuticals/AEROPERL-300-Pharma/Pages/default.aspx, 1 page.
European Communication pursuant to Article 94(3) dated Dec. 1, 2017, for European Patent Application 15184628.4, nine pages.
European Communication, Provision of the minutes in accordance with Rule 124(4) dated Dec. 11, 2017, for European Patent Application No. 09739981.0.
Final Board Decision issued in Chinese Patent Application No. 201310447258.1, dated Dec. 14, 2017, 49 pages (with English translation).
CN Office Action in Chinese Appln. No. 2015104083760, dated Jun. 6, 2018, 23 pages (with English Translation).

* cited by examiner

USE OF SOLID CARRIER PARTICLES TO IMPROVE THE PROCESSABILITY OF A PHARMACEUTICAL AGENT

PRIORITY OF INVENTION

This application claims priority to U.S. Provisional Patent Application No. 61/049,935 filed 2 May 2008; to U.S. Provisional Patent Application No. 61/150,655 filed 6 Feb. 2009; and to U.S. Provisional Patent Application No. 61/150,652 filed 6 Feb. 2009. The entire content of each of these applications is hereby incorporated herein by reference.

BACKGROUND OF THE INVENTION

International patent application publication number WO 03/037379 discusses the use of granular materials based on pyrogenically produced silicone dioxide in certain specific pharmaceutical compositions. Adsorbates consisting of the granular materials and a further substance (e.g. a pharmaceutically active constituent) are also discussed.

International patent application publication number WO 2008/010921 describes compounds and pharmaceutical compositions that improve the pharmacokinetics of a co-administered drug by inhibiting cytochrome P450 monooxygenase. One such inhibitor is the compound of formula (I).

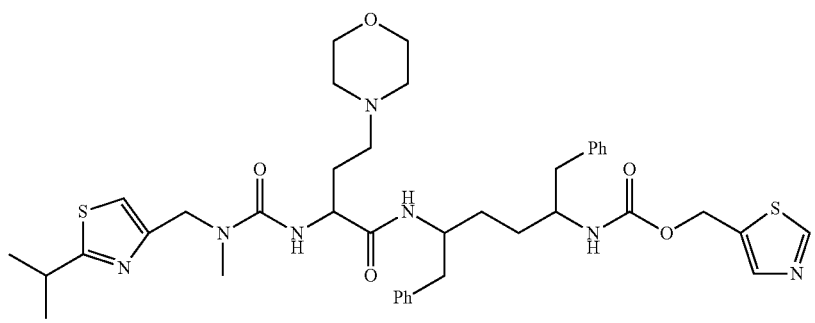

Unfortunately, the solid state properties of the compound of formula (I) make it difficult to handle and process on a large scale. For example, its low glass transition temperature, hygroscopicity, and lack of crystallinity, as well as its non free-flowing nature make it particularly difficult to process and to formulate (e.g. as a tablet).

There is currently a need for improved formulations of the compound of formula (I), and a need for improved methods for processing and formulating the compound of formula (I) on a commercial scale. Such improved processes and methods will eliminate one or more of the current difficulties associated with processing and formulating the compound.

SUMMARY OF THE INVENTION

When the compound of formula (I) or a pharmaceutically acceptable salt thereof is combined with certain specific solid carrier particles (e.g. silica derivatives), the resulting combination possesses unexpectedly improved physical properties. For example, in spite of the fact that both the compound of formula (I) and the starting colloidal silicon dioxide materials in Example 2 are hygroscopic in nature, the resulting combination has comparatively low hygroscopicity. Additionally, the resulting combination is a free-flowing powder, with high loading values for the compound of formula (I), acceptable physical and chemical stability, rapid drug release properties, and excellent compressibility. Thus, the resulting combination can readily be processed into solid dosage forms (e.g. tablets), which possess good drug release properties, low tablet friability, good chemical and physical stability, and a low amount of residual solvents. The compositions of the invention represent a significant advance that facilitates the commercial development of the compound of formula (I) for use in treating viral infections such as HIV.

Accordingly, in one embodiment, the invention provides a composition comprising, a plurality of solid carrier particles that each have a surface and/or pores; and a compound of formula (I):

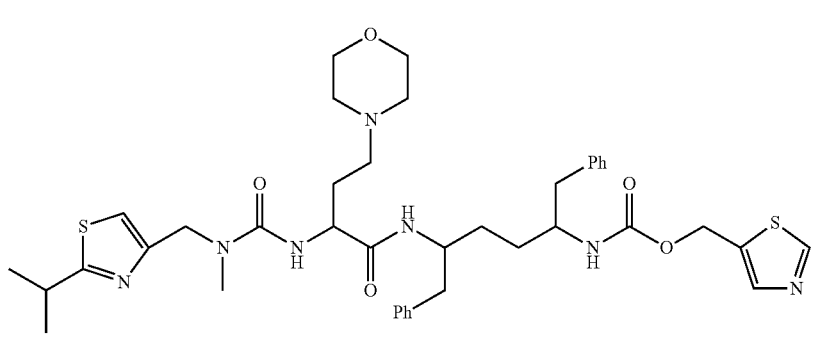

or a pharmaceutically acceptable salt of thereof in the pores or on the surface of the solid carrier particles.

In another embodiment the invention also provides a method comprising combining a compound of formula (I), a suitable solvent, and a plurality of solid carrier particles to provide a mixture. Such a mixture is useful for preparing pharmaceutical formulations that comprise the compound of formula (I).

In another embodiment the invention provides a tablet comprising: 1) a compound of formula (I) and 2) a plurality of solid carrier particles.

In another embodiment the invention provides a pharmaceutical composition that comprise a plurality of solid carrier particles; a compound of formula (Ia); tenofovir disoproxil fumarate; emtricitabine; and elvitegravir.

In another embodiment, the invention provides methods and intermediate mixtures that are useful for preparing the compositions of the invention.

The invention also provides a method for inhibiting cytochrome P-450 comprising administering a pharmaceutically acceptable composition of the invention to a mammal (e.g. a human) in need of such treatment.

The invention provides a composition of the invention for use in medical therapy (e.g. for use in inhibiting cytochrome p-450 in a mammal), as well as the use of a composition of the invention for the manufacture of a medicament useful for inhibiting cytochrome P-450 in a mammal, such as a human.

In another embodiment the invention also provides compositions prepared by the methods described herein.

DETAILED DESCRIPTION OF THE INVENTION

Figure 1:
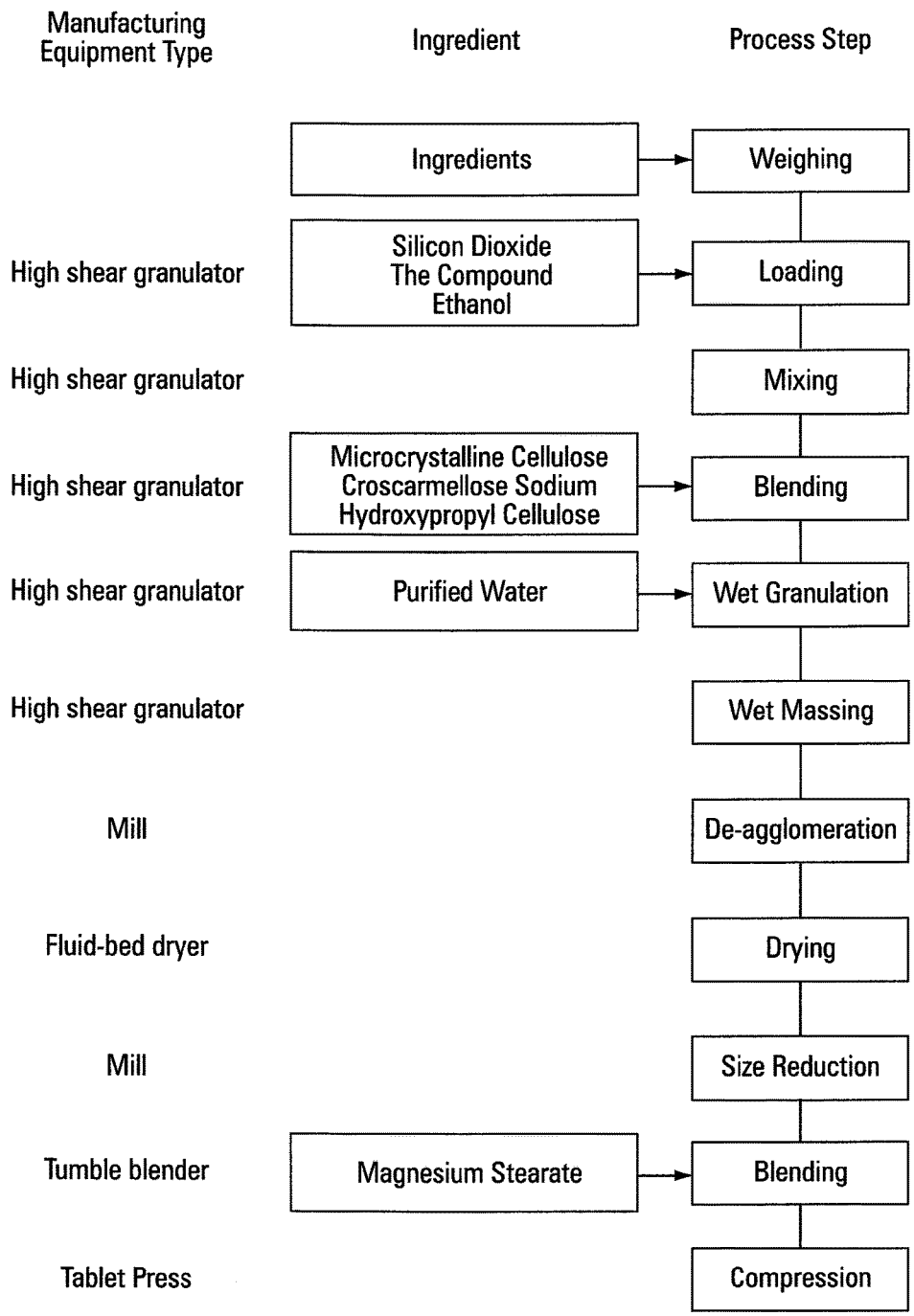
FIG. 1 Illustrates the preparation of a pharmaceutical formulation of the invention as well as processing methods of the invention.

It will be appreciated by those skilled in the art that compounds of formula (I) may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of formula (I), which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

In one embodiment of the invention, the compound of formula (I) that is incorporated into the compositions of the invention is enriched with a stereoisomer of formula (Ia):

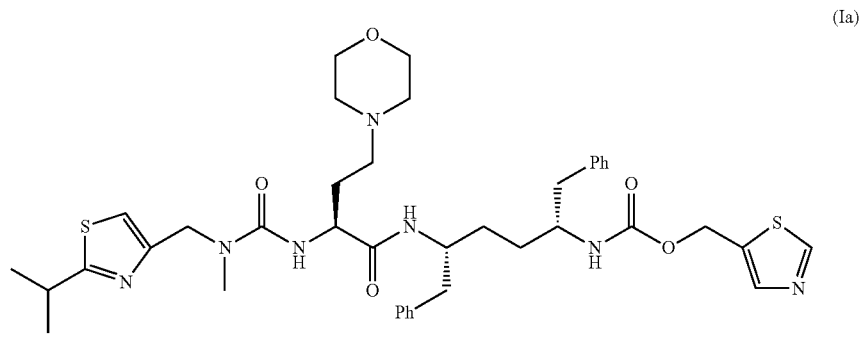 [SMILES: CC(C)c1nc(CN(C)C(=O)N[C@@H](CCN2CCOCC2)C(=O)N[C@H](CC[C@H](Cc2ccccc2)NC(=O)OCc2cncs2)Cc2ccccc2)cs1]

(Ia)

which is thiazol-5-ylmethyl (2R,5R)-5-((S)-2-(3((2-isopropylthiazol-4-yl)methyl)-3-methylureido)-4-morpholinobutanamido)-1,6-diphenylhexan-2-ylcarbamate. In one embodiment the compound of formula (I) has an enriched concentration of 85±5% of the stereoisomer of formula (Ia). In another embodiment the compound of formula (I) has an enriched concentration of 90±5% of the stereoisomer of formula (Ia). In another embodiment the compound of formula (I) has an enriched concentration of 95±2% of the stereoisomer of formula (Ia). In another embodiment the compound of formula (I) has an enriched concentration of 99±1% of the stereoisomer of formula (Ia). In another embodiment the compound of formula (I) is the pure the stereoisomer of formula (Ia).

Solid Carriers

The compound of formula (I) can be combined with any suitable solid carrier, provided the resulting combination has physical properties that allow it to be more easily formulated than the parent compound. For example, suitable solid carriers include kaolin, bentonite, hectorite, colloidal magnesium-aluminum silicate, silicon dioxide, magnesium trisilicate, aluminum hydroxide, magnesium hydroxide, magnesium oxide and talc. In one embodiment of the invention, the solid carrier can comprise calcium silicate (such as Zeopharm), or magnesium aluminometasilicate (such as Neusilin). As used herein, "loaded" on a solid carrier includes, but is not limited to a compound of formula (I) being coated in the pores and on the surface of a solid carrier.

Suitable silica derivatives for use in the compositions of the invention and methods for preparing such silica derivatives include those that are described in international patent application publication number WO 03/037379 and the references cited therein. Typically, these silica derivatives comprise a granular hydrophilic fumed silica that has a mean particle diameter of 10 to 120 micron and a BET surface area of 40 to 400 m$^2$/g (determined according to DIN 66 131 with nitrogen). The silica derivatives also typically have a pore volume of about 0.5 to 2.5 mL/g, wherein less than about 5% of the overall pore volume has a pore diameter of less than about 5 nm, the remainder being mesopores and macropores. Additionally, the silica derivatives typically have a pH in the range of about 3.6 to about 8.5 and a tamped density of about 220 to about 700 g/L.

A specific silica material that is particularly useful in the compositions and methods of the invention is AEROPERL® 300 (fumed silica), which is available from Evonik Degussa AG, Dusseldorf, Germany. However, other materials having physical and chemical properties similar to the silica materials described herein can also be used.

In one embodiment of the invention the silica particles have a mean grain diameter of 20-40 micron. In one embodiment of the invention the silica particles have a BET surface area of at least 150 m$^2$/g. In one embodiment of the invention the silica particles have a BET surface area of at least 200 m$^2$/g. In one embodiment of the invention the silica particles have a BET surface area of at least 250 m$^2$/g. In one embodiment of the invention the silica particles have a BET surface area of at least 275 m$^2$/g.

In the compositions of the invention, the compound of formula (I) is typically coated in the pores and on the surface of the fumed silica particles. It has been determined that up to about 60% (w/w) of the compound of formula (I) can typically be loaded on these silica particles. This high loading capacity is beneficial for pharmaceutical applications. In one embodiment of the invention the weight percentage of the compound of formula (I) to the silica particles is 20%±15%. In one embodiment of the invention the weight percentage of the compound of formula (I) to the silica particles is 50%±10%. In one embodiment of the invention the weight percentage of the compound of formula (I) to the silica particles is 45%±15%. In one embodiment of the invention the (weight of the compound of Formula (I)) divided by the (weight of the solid carrier, e.g. the silica derivative) in a composition is from about 0.8 to about 1.2. In another embodiment of the invention the (weight of the compound of Formula (I)) divided by the (weight of the solid carrier, e.g. the silica derivative) in a composition is 1.0±0.5.

The compositions of the invention that are suitable for administration as pharmaceuticals will typically comprise one or more pharmaceutically acceptable excipients.

Loading

The compound of formula (I) can be loaded on the solid carrier using any suitable method. For example the compound of formula (I) can be loaded on the solid carrier by:
  a) spraying a solution of the compound (e.g. a solution of the compound in an alcohol solvent such as ethanol) onto the solid carrier, for example, as described in Example 1 below;
  b) combining the compound of formula (I), a suitable solvent (e.g. a volatile solvent such as dichloromethane), and the solid carrier; evaporating the solvent; and isolating the resulting solid material; or
  c) combining the compound of formula (I) and a suitable volatile solvent (e.g. a halogenated hydrocarbon such as dichloromethane), and the solid carrier; adding an antisolvent (e.g. a highly non-polar solvent such as hexanes or heptane) and isolating the resulting solid material (as illustrated in Example 4).

FIG. 1 illustrates the preparation of a pharmaceutical formulation that comprises a compound of formula (I) according to a method of the invention. The compound of formula (I) can be combined with a suitable solvent and a plurality of silica particles to provide a mixture. Optionally, the compound of formula (I) can be combined with the suitable solvent with concurrent mixing. Typically, the weight percentage of the compound of formula (I) to the silica particles prior to combining is about is 50%±10%. In one embodiment of the invention the weight percentage of the compound of formula (I) to the silica particles prior to combining is about 20%±10%. In another embodiment of the invention the weight percentage of the compound of formula (I) to the silica particles prior to combining is about 30%±10%. Any solvent in which the compound of formula (I) is soluble can be used. Typically, the solvent comprises a volatile organic solvent, such as, for example, a ($C_1$-$C_6$) alcohol (e.g. ethanol).

As illustrated in Example 4 below, a compound of formula (I) can also be loaded into a silica material by dissolving the compound in a suitable solvent to provide a solution comprising Compound I; adding silica particles to the solution to provide a mixture; optionally agitating or stirring the mixture; adding an antisolvent to the mixture; and isolating the solid mixture that comprises the compound of formula (I) on the silica particles. Suitable solvents include organic solvents such as ketones (e.g. acetone), alcohols (e.g. ethanol) and halogenated hydrocarbons (e.g. dichloromethane). Suitable antisolvents include highly non-polar solvents (e.g. hexane or heptane). The final solid mixture can be isolated by any suitable separation technique (e.g. filtration).

One or more pharmaceutically acceptable excipients can be combined with the mixture to provide a second mixture. These pharmaceutically acceptable excipients can include fillers, binders, and disintegrants. In order to improve the processability of the mixture in the subsequent aqueous granulation process, it can be beneficial to select fillers and disintegrants that are compatible with this aqueous process. For example microcrystalline cellulose (filler) and croscarmellose sodium (disintegrant) were found to be particularly compatible with the subsequent aqueous granulation process. Hydroxypropyl cellulose (binder) was also found to be particularly compatible with the subsequent granulation process. In one embodiment of the invention the weight percentage of microcrystalline cellulose to the total weight of the second mixture is about 50%±20%. In one embodiment of the invention the weight percentage of hydroxypropyl cellulose to the total weight of the second mixture is 2%±1%. In one embodiment of the invention the weight percentage of croscarmellose sodium is 5%±2%. Following addition of the pharmaceutically acceptable excipients, the second mixture can be mixed, for example, using a mechanical mixer, such as a high shear granulator (Niro-Fielder, model PMA-25).

Water can be added to the second mixture to provide a wet granulate, which can subsequently be de-agglomerated, e.g. with a 20 mesh sieve. Drying, for example using a fluid bed dryer (Fluid Air, model 20), provides a dried material that comprises solid particles. In one embodiment the dried material has less than about 10.0% moisture content as determined by loss on drying (LOD). In another embodiment the dried material has less than about 5.0% moisture content as determined by loss on drying (LOD). In another embodiment the dried material has less than about 1.0% moisture content as determined by loss on drying (LOD).

The size of these particles can be reduced, e.g. using a 40 mesh sieve or a suitable mill (Quadro CoMil, model 197/S) to provide a third mixture.

A suitable pharmaceutically acceptable lubricant/glidant (e.g. magnesium stearate, stearic acid, calcium stearate, zinc stearate, or pregelatinized starch) can be combined with the third mixture to provide a fourth mixture. In one embodiment the weight percentage of magnesium stearate to the total weight of the fourth mixture is 1%±0.5%.

In one embodiment, the invention provides a composition prepared by the methods described herein. The invention also provides a product prepared by any of the process steps described herein.

Pharmaceutical Formulations Comprising the Compound of Formula (I)

In one embodiment the invention provides pharmaceutical compositions comprising a compound of formula (I) that can be administered to a mammalian host, such as a human patient, in a variety of forms adapted to the chosen route of administration (e.g. orally).

Thus, the compositions of the invention may be administered in combination with one or more pharmaceutically acceptable ingredients such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations will typically contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as hydroxypropyl cellulose, povidone, or hydroxypropyl methylcellulose; fillers, such as microcrystalline cellulose, pregelatinized starch, starch, mannitol, or lactose monohydrate; a disintegrating agent such as croscarmellose sodium, cross-linked povidone, or sodium starch glycolate; a lubricant such as magnesium stearate, stearic acid, or other metallic stearates; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, polymers, wax, shellac or sugar and the like. Of course, any material used in preparing any unit dosage form will typically be pharmaceutically acceptable and substantially non-toxic in the amounts employed. In addition, the compositions of the invention may be incorporated into sustained-release preparations and devices.

The compositions of the invention can also be administered topically, e.g., transdermally, buccally, or sublingually. Accordingly, the invention also provides pharmaceutical compositions that are formulated for such routes of topical administration.

Useful dosages of the compounds of formula I can be determined by comparing their in vitro activity, and in vivo activity in animal models. Methods for the extrapolation of effective dosages in mice, and other animals, to humans are known to the art.

The amount of a composition of the invention required for use in treatment will vary with the route of administration, the nature of the condition being treated and the age and condition of the patient and will be ultimately at the discretion of the attendant physician or clinician.

In general, however, a suitable dose of the compound of formula (I) will be in the range of from about 0.05 to about 100 mg/kg, e.g., from about 0.05 to about 50 mg/kg of body weight per day, preferably in the range of 0.05 to 10 mg/kg/day, most preferably in the range of 0.05 to 5 mg/kg/day.

The compound is conveniently formulated in unit dosage form; for example, containing about 5 to 500 mg, about 5 to 250 mg, or about 10 to 100 mg of the compound of formula (I). In one embodiment, the invention provides a composition comprising about 5, about 25, or about 100 mg of a compound of formula (I) formulated in a unit dosage form that further comprises a solid carrier particles (e.g. silica particles), and one or more pharmaceutically acceptable carriers.

The ability of a compound of formula (I) to inhibit cytochrome P-450 can be evaluated as described in international patent application publication number WO 2008/010921.

Combination Formulations

As discussed in international patent application publication number WO 2008/010921, the compound of formula (I) improves the pharmacokinetics of a co-administered drug, e.g. by inhibiting cytochrome P-450 monooxygenase. Accordingly, in another embodiment, the pharmaceutical compositions of the invention can further comprise at least one additional therapeutic agent.

The additional therapeutic agent can be any agent having a therapeutic effect when used in combination with the compound of the present invention. For example, the additional therapeutic agent used in combination with the compound of formula (I) can be any agent that is accessible to oxidative metabolism by cytochrome P450 enzymes, especially cytochrome P450 monooxygenase, e.g., 1A2, 2B6, 2C8, 2C19, 2C9, 2D6, 2E1, 3A4, 5, 7, etc.

In one example, the additional therapeutic agent can be any anti-viral agent, e.g., anti-HIV, anti-HCV, etc., anti-bacterial agent, anti-fungal agent, immuno-modulator, e.g. immunosuppressant, anti-neoplastic agent, chemotherapeutic agent, agents useful for treating cardiovascular conditions, neurological conditions, etc.

In another example, the additional therapeutic agent can be any proton pump inhibitor, anti-epileptics, NSAID, oral hypoglycemic agent, angiotensin II receptor antagonist, sulfonylurea, beta blocker, antidepressant, antipsychotic, or anesthetic, or a combination thereof.

In another example, the additional therapeutic agent can be any 1) macrolide antibiotic, e.g., clarithromycin, erythromycin, telithromycin, 2) anti-arrhythmic, e.g., quinidine=>3-OH, 3) benzodiazepine, e.g., alprazolam, diazepam=>3OH, midazolam, triazolam, 4) immune modulator, e.g., cyclosporine, tacrolimus (FK506), 5) HIV anti-viral, e.g., indinavir, nelfinavir, ritonavir, saquinavir, 6) prokinetic, e.g., cisapride, 7) antihistamine, e.g., astemizole, chlorpheniramine, terfenidine, 8) calcium channel blocker, e.g., amlodipine, diltiazem, felodipine, lercanidipine, nifedipine, nisoldipine, nitrendipine, verapamil, 9) HMG CoA reductase inhibitor, e.g., atorvastatin, cerivastatin, lovastatin, simvastatin, or 10) steroid 6beta-OH, e.g., estradiol, hydrocortisone, progesterone, testosterone.

In another example, the additional therapeutic agent can be alfentanyl, aprepitant, aripiprazole, buspirone, cafergot, caffeine, TMU, cilostazol, cocaine, codeine-N-demethylation, dapsone, dextromethorphan, docetaxel, domperidone, eplerenone, fentanyl, finasteride, gleevec, haloperidol, irinotecan, LAAM, lidocaine, methadone, nateglinide, ondansetron, pimozide, propranolol, quetiapine, quinine, salmeterol, sildenafil, sirolimus, tamoxifen, paclitaxel, terfenadine, trazodone, vincristine, zaleplon, or zolpidem or a combination thereof.

In one specific embodiment, the invention provides a pharmaceutical composition comprising, 1) a compound of formula (I), 2) a plurality of solid carrier particles, and 3) at least one additional therapeutic agent selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, non-nucleoside inhibitors of HCV, CCR5 inhibitors, and combinations thereof, and 4) a pharmaceutically acceptable excipient.

In one specific embodiment, the invention provides a pharmaceutical composition comprising, 1) a compound of formula (I), 2) a plurality of silica particles that each have a surface and pores, and that have a mean particle diameter of 10 to 120 micron and a BET surface area of 40 to 400 $m^2/g$, and 3) at least one additional therapeutic agent selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, non-nucleoside inhibitors of HCV, CCR5 inhibitors, and combinations thereof, and 4) a pharmaceutically acceptable excipient.

In another embodiment, the present invention provides pharmaceutical compositions comprising 1) a compound of formula (I), 2) a plurality of solid carrier particles, and 3) at least one additional therapeutic agent selected from the group consisting of amprenavir, atazanavir, fosamprenavir, indinavir, lopinavir, ritonavir, nelfinavir, saquinavir, tipranavir, brecanavir, darunavir, TMC-126, TMC-114, mozenavir (DMP-450), JE-2147 (AG1776), L-756423, RO0334649, KNI-272, DPC-681, DPC-684, GW640385X, DG17, PPL-100, DG35, AG 1859, capravirine, emivirine, delaviridine, efavirenz, nevirapine, (+) calanolide A, etravirine, GW5634, DPC-083, DPC-961, DPC-963, MIV-150, TMC-120, TMC-278 (rilpivirene), BILR 355 BS, VRX 840773, UK-453061, RDEA806, zidovudine, emtricitabine, didanosine, stavudine, zalcitabine, lamivudine, abacavir, amdoxovir, elvucitabine, alovudine, MIV-210, Racivir (±-FTC), D-d4FC, phosphazide, fozivudine tidoxil, apricitibine AVX754, amdoxovir, KP-1461, and fosalvudine tidoxil (formerly HDP 99.0003), tenofovir disoproxil fumarate, adefovir dipivoxil, GS-9131, curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), L-870812, L-870810, MK-0518 (raltegravir), elvitegravir, BMS-538158, GSK364735C, BMS-707035, MK-2048, BA 011, enfuvirtide, sifuvirtide, FB006M, TRI-1144, AMD-070, SP01A, BMS-488043, BlockAide/CR, immunitin, benzimidazole derivatives, benzo-1,2,4-thiadiazine derivatives, phenylalanine derivatives, aplaviroc, vicriviroc, and maraviroc, cyclosporine, FK-506, rapamycin, paclitaxel, taxotere, clarithromycin, A-77003, A-80987, MK-639, saquinavir, VX-478, AG1343, DMP-323, XM-450, BILA 2011 BS, BILA 1096 BS, BILA 2185 BS, BMS 186,318, LB71262, SC-52151, SC-629 (N,N-dimethylglycyl-N-(2-hydroxy-3-(((4-methoxyphenyl)sulphonyl)(2-methylpropyl)amino)-1-(phenylmethyl)propyl)-3-methyl-L-valinamide), KNI-272, CGP 53437, CGP 57813 and U-103017; and 4) a pharmaceutically acceptable carrier or excipient.

In another embodiment, the present invention provides pharmaceutical compositions comprising 1) a compound of formula (I), 2) a plurality of silica particles that each have a surface and pores, and that have a mean particle diameter of 10 to 120 micron and a BET surface area of 40 to 400 $m^2/g$, and 3) at least one additional therapeutic agent selected from the group consisting of amprenavir, atazanavir, fosamprenavir, indinavir, lopinavir, ritonavir, nelfinavir, saquinavir, tipranavir, brecanavir, darunavir, TMC-126, TMC-114, mozenavir (DMP-450), JE-2147 (AG1776), L-756423, RO0334649, KNI-272, DPC-681, DPC-684, GW640385X, DG17, PPL-100, DG35, AG 1859, capravirine, emivirine, delaviridine, efavirenz, nevirapine, (+) calanolide A, etravirine, GW5634, DPC-083, DPC-961, DPC-963, MIV-150, TMC-120, TMC-278 (rilpivirene), BILR 355 BS, VRX 840773, UK-453061, RDEA806, zidovudine, emtricitabine, didanosine, stavudine, zalcitabine, lamivudine, abacavir, amdoxovir, elvucitabine, alovudine, MIV-210, Racivir (±-FTC), D-d4FC, phosphazide, fozivudine tidoxil, apricitibine AVX754, amdoxovir, KP-1461, and fosalvudine tidoxil (formerly HDP 99.0003), tenofovir disoproxil fumarate, adefovir dipivoxil, GS-9131, curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), L-870812, L-870810, MK-0518 (raltegravir), elvitegravir, BMS-538158, GSK364735C, BMS-707035, MK-2048, BA 011, enfuvirtide, sifuvirtide, FB006M, TRI-1144, AMD-070, SP01A, BMS-488043, BlockAide/CR, immunitin, benzimidazole derivatives, benzo-1,2,4-thiadiazine derivatives, phenylalanine derivatives, aplaviroc, vicriviroc, and maraviroc, cyclosporine, FK-506, rapamycin, paclitaxel, taxotere, clarithromycin, A-77003, A-80987, MK-639, saquinavir, VX-478, AG1343, DMP-323, XM-450, BILA 2011 BS, BILA 1096 BS, BILA 2185 BS, BMS 186,318, LB71262, SC-52151, SC-629 (N,N-dimethylglycyl-N-(2-hydroxy-3-(((4-methoxyphenyl)sulphonyl)(2-methylpropyl)amino)-1-(phenylmethyl)propyl)-3-methyl-L-valinamide), KNI-272, CGP 53437, CGP 57813 and U-103017; and 4) a pharmaceutically acceptable carrier or excipient.

In another embodiment, the present invention provides pharmaceutical compositions comprising 1) a compound of formula (I), 2) a plurality of solid carrier particles, and 3) two or three additional therapeutic agents. For example, additional therapeutic agents selected from the classes of HIV protease inhibitors, HIV non-nucleoside inhibitors of reverse transcriptase, HIV nucleoside inhibitors of reverse transcriptase, HIV nucleotide inhibitors of reverse transcriptase, and HIV integrase inhibitors. The two or three additional therapeutic agents can be different therapeutic agents selected from the same class of therapeutic agents, or they can be selected from different classes of therapeutic agents.

In another embodiment, the present invention provides pharmaceutical compositions comprising 1) a compound of formula (I), 2) a plurality of silica particles that each have a surface and pores, and that have a mean particle diameter of 10 to 120 micron and a BET surface area of 40 to 400 m$^2$/g, and 3) two or three additional therapeutic agents. For example, additional therapeutic agents selected from the classes of HIV protease inhibitors, HIV non-nucleoside inhibitors of reverse transcriptase, HIV nucleoside inhibitors of reverse transcriptase, HIV nucleotide inhibitors of reverse transcriptase, and HIV integrase inhibitors. The two or three additional therapeutic agents can be different therapeutic agents selected from the same class of therapeutic agents, or they can be selected from different classes of therapeutic agents.

In another embodiment, the invention provides pharmaceutical compositions that comprise a plurality of solid carrier particles, and a ternary combination of agents selected from Formula (I)/tenofovir disoproxil fumarate/GS-9131, Formula (I)/tenofovir disoproxil fumarate/emtricitabine, Formula (I)/tenofovir disoproxil fumarate/elvitegravir, Formula (I)/tenofovir disoproxil fumarate/efavrenz, Formula (I)/tenofovir disoproxil fumarate/atazanavir, Formula (I)/tenofovir disoproxil fumarate/darunavir, Formula (I)/tenofovir disoproxil fumarate/raltegravir, Formula (I)/tenofovir disoproxil fumarate/rilpivirine, Formula (I)/GS-9131/emtricitabine, Formula (I)/GS-9131/elvitegravir, Formula (I)/GS-9131/efavrenz, Formula (I)/GS-9131/atazanavir, Formula (I)/GS-9131/darunavir, Formula (I)/GS-9131/raltegravir, Formula (I)/GS-9131/rilpivirine, Formula (I)/emtricitabine/elvitegravir, Formula (I)/emtricitabine/efavrenz, Formula (I)/emtricitabine/atazanavir, Formula (I)/emtricitabine/darunavir, Formula (I)/emtricitabine/raltegravir, Formula (I)/emtricitabine/rilpivirine, Formula (I)/elvitegravir/efavrenz, Formula (I)/elvitegravir/atazanavir, Formula (I)/elvitegravir/darunavir, Formula (I)/elvitegravir/raltegravir, Formula (I)/elvitegravir/rilpivirine, Formula (I)/efavrenz/atazanavir, Formula (I)/efavrenz/darunavir, Formula (I)/efavrenz/raltegravir, Formula (I)/efavrenz/rilpivirine, Formula (I)/atazanavir/darunavir, Formula (I)/atazanavir/raltegravir, Formula (I)/atazanavir/rilpivirine, Formula (I)/darunavir/raltegravir, Formula (I)/darunavir/rilpivirine, and Formula (I)/raltegravir/rilpivirine.

In another embodiment, the invention provides pharmaceutical compositions that comprise a plurality of silica particles that each have a surface and pores, and that have a mean particle diameter of 10 to 120 micron and a BET surface area of 40 to 400 m$^2$/g, and a ternary combination of agents selected from Formula (I)/tenofovir disoproxil fumarate/GS-9131, Formula (I)/tenofovir disoproxil fumarate/emtricitabine, Formula (I)/tenofovir disoproxil fumarate/elvitegravir, Formula (I)/tenofovir disoproxil fumarate/efavrenz, Formula (I)/tenofovir disoproxil fumarate/atazanavir, Formula (I)/tenofovir disoproxil fumarate/darunavir, Formula (I)/tenofovir disoproxil fumarate/raltegravir, Formula (I)/tenofovir disoproxil fumarate/rilpivirine, Formula (I)/GS-9131/emtricitabine, Formula (I)/GS-9131/elvitegravir, Formula (I)/GS-9131/efavrenz, Formula (I)/GS-9131/atazanavir, Formula (I)/GS-9131/darunavir, Formula (I)/GS-9131/raltegravir, Formula (I)/GS-9131/rilpivirine, Formula (I)/emtricitabine/elvitegravir, Formula (I)/emtricitabine/efavrenz, Formula (I)/emtricitabine/atazanavir, Formula (I)/emtricitabine/darunavir, Formula (I)/emtricitabine/raltegravir, Formula (I)/emtricit- abine/rilpivirine, Formula (I)/elvitegravir/efavrenz, Formula (I)/elvitegravir/atazanavir, Formula (I)/elvitegravir/darunavir, Formula (I)/elvitegravir/raltegravir, Formula (I)/elvitegravir/rilpivirine, Formula (I)/efavrenz/atazanavir, Formula (I)/efavrenz/darunavir, Formula (I)/efavrenz/raltegravir, Formula (I)/efavrenz/rilpivirine, Formula (I)/atazanavir/darunavir, Formula (I)/atazanavir/raltegravir, Formula (I)/atazanavir/rilpivirine, Formula (I)/darunavir/raltegravir, Formula (I)/darunavir/rilpivirine, and Formula (I)/raltegravir/rilpivirine.

In another embodiment, the invention provides pharmaceutical compositions that comprise a plurality of solid carrier particles, and a quaternary combination of agents selected from Formula (I)/tenofovir disoproxil fumarate/GS-9131/emtricitabine, Formula (I)/tenofovir disoproxil fumarate/GS-9131/elvitegravir, Formula (I)/tenofovir disoproxil fumarate/GS-9131/efavrenz, Formula (I)/tenofovir disoproxil fumarate/GS-9131/atazanavir, Formula (I)/tenofovir disoproxil fumarate/GS-9131/darunavir, Formula (I)/tenofovir disoproxil fumarate/GS-9131/raltegravir, Formula (I)/tenofovir disoproxil fumarate/GS-9131/rilpivirine, Formula (I)/tenofovir disoproxil fumarate/emtricitabine/elvitegravir, Formula (I)/tenofovir disoproxil fumarate/emtricitabine/efavrenz, Formula (I)/tenofovir disoproxil fumarate/emtricitabine/atazanavir, Formula (I)/tenofovir disoproxil fumarate/emtricitabine/darunavir, Formula (I)/tenofovir disoproxil fumarate/emtricitabine/raltegravir, Formula (I)/tenofovir disoproxil fumarate/emtricitabine/rilpivirine, Formula (I)/tenofovir disoproxil fumarate/elvitegravir/efavrenz, Formula (I)/tenofovir disoproxil fumarate/elvitegravir/atazanavir, Formula (I)/tenofovir disoproxil fumarate/elvitegravir/darunavir, Formula (I)/tenofovir disoproxil fumarate/elvitegravir/raltegravir, Formula (I)/tenofovir disoproxil fumarate/elvitegravir/rilpivirine, Formula (I)/tenofovir disoproxil fumarate/efavrenz/atazanavir, Formula (I)/tenofovir disoproxil fumarate/efavrenz/darunavir, Formula (I)/tenofovir disoproxil fumarate/efavrenz/raltegravir, Formula (I)/tenofovir disoproxil fumarate/efavrenz/rilpivirine, Formula (I)/tenofovir disoproxil fumarate/atazanavir/darunavir, Formula (I)/tenofovir disoproxil fumarate/atazanavir/raltegravir, Formula (I)/tenofovir disoproxil fumarate/atazanavir/rilpivirine, Formula (I)/tenofovir disoproxil fumarate/darunavir/raltegravir, Formula (I)/tenofovir disoproxil fumarate/darunavir/rilpivirine, Formula (I)/tenofovir disoproxil fumarate/raltegravir/rilpivirine, Formula (I)/GS-9131/emtricitabine/elvitegravir, Formula (I)/GS-9131/emtricitabine/efavrenz, Formula (I)/GS-9131/emtricitabine/atazanavir, Formula (I)/GS-9131/emtricitabine/darunavir, Formula (I)/GS-9131/emtricitabine/raltegravir, Formula (I)/GS-9131/emtricitabine/rilpivirine, Formula (I)/GS-9131/elvitegravir/efavrenz, Formula (I)/GS-9131/elvitegravir/atazanavir, Formula (I)/GS-9131/elvitegravir/darunavir, Formula (I)/GS-9131/elvitegravir/raltegravir, Formula (I)/GS-9131/elvitegravir/rilpivirine, Formula (I)/GS-9131/efavrenz/atazanavir, Formula (I)/GS-9131/efavrenz/darunavir, Formula (I)/GS-9131/efavrenz/raltegravir, Formula (I)/GS-9131/efavrenz/rilpivirine, Formula (I)/GS-9131/atazanavir/darunavir, Formula (I)/GS-9131/atazanavir/raltegravir, Formula (I)/GS-9131/atazanavir/rilpivirine, Formula (I)/GS-9131/darunavir/raltegravir, Formula (I)/GS-9131/darunavir/rilpivirine, Formula (I)/GS-9131/raltegravir/rilpivirine, Formula (I)/emtricitabine/elvitegravir/efavrenz, Formula (I)/emtricitabine/elvitegravir/atazanavir, Formula (I)/emtricitabine/elvitegravir/darunavir, Formula (I)/emtricitabine/elvitegravir/raltegravir, Formula (I)/emtricitabine/elvitegravir/rilpivirine, Formula (I)/emtricitabine/efavrenz/atazanavir, Formula (I)/emtricitabine/ efavrenz/darunavir, Formula (I)/emtricitabine/efavrenz/raltegravir, Formula (I)/emtricitabine/efavrenz/rilpivirine, Formula (I)/emtricitabine/atazanavir/darunavir, Formula (I)/emtricitabine/atazanavir/raltegravir, Formula (I)/emtricitabine/atazanavir/rilpivirine, Formula (I)/emtricitabine/darunavir/raltegravir, Formula (I)/emtricitabine/darunavir/rilpivirine, Formula (I)/emtricitabine/raltegravir/rilpivirine, Formula (I)/elvitegravir/efavrenz/atazanavir, Formula (I)/elvitegravir/efavrenz/darunavir, Formula (I)/elvitegravir/efavrenz/raltegravir, Formula (I)/elvitegravir/efavrenz/rilpivirine, Formula (I)/elvitegravir/atazanavir/darunavir, Formula (I)/elvitegravir/atazanavir/raltegravir, Formula (I)/elvitegravir/atazanavir/rilpivirine, Formula (I)/elvitegravir/darunavir/raltegravir, Formula (I)/elvitegravir/darunavir/rilpivirine, Formula (I)/elvitegravir/raltegravir/rilpivirine, Formula (I)/efavrenz/atazanavir/darunavir, Formula (I)/efavrenz/atazanavir/raltegravir, Formula (I)/efavrenz/atazanavir/rilpivirine, Formula (I)/efavrenz/darunavir/raltegravir, Formula (I)/efavrenz/darunavir/rilpivirine, Formula (I)/efavrenz/raltegravir/rilpivirine, Formula (I)/atazanavir/darunavir/raltegravir, Formula (I)/atazanavir/darunavir/rilpivirine, and Formula (I)/darunavir/raltegravir/rilpivirine.

In another embodiment, the invention provides pharmaceutical compositions that comprise a plurality of silica particles that each have a surface and pores, and that have a mean particle diameter of 10 to 120 micron and a BET surface area of 40 to 400 m$^2$/g., and a quaternary combination of agents selected from Formula (I)/tenofovir disoproxil fumarate/GS-9131/emtricitabine, Formula (I)/tenofovir disoproxil fumarate/GS-9131/elvitegravir, Formula (I)/tenofovir disoproxil fumarate/GS-9131/efavrenz, Formula (I)/tenofovir disoproxil fumarate/GS-9131/atazanavir, Formula (I)/tenofovir disoproxil fumarate/GS-9131/darunavir, Formula (I)/tenofovir disoproxil fumarate/GS-9131/raltegravir, Formula (I)/tenofovir disoproxil fumarate/GS-9131/rilpivirine, Formula (I)/tenofovir disoproxil fumarate/emtricitabine/elvitegravir, Formula (I)/tenofovir disoproxil fumarate/emtricitabine/efavrenz, Formula (I)/tenofovir disoproxil fumarate/emtricitabine/atazanavir, Formula (I)/tenofovir disoproxil fumarate/emtricitabine/darunavir, Formula (I)/tenofovir disoproxil fumarate/emtricitabine/raltegravir, Formula (I)/tenofovir disoproxil fumarate/emtricitabine/rilpivirine, Formula (I)/tenofovir disoproxil fumarate/elvitegravir/efavrenz, Formula (I)/tenofovir disoproxil fumarate/elvitegravir/atazanavir, Formula (I)/tenofovir disoproxil fumarate/elvitegravir/darunavir, Formula (I)/tenofovir disoproxil fumarate/elvitegravir/raltegravir, Formula (I)/tenofovir disoproxil fumarate/elvitegravir/rilpivirine, Formula (I)/tenofovir disoproxil fumarate/efavrenz/atazanavir, Formula (I)/tenofovir disoproxil fumarate/efavrenz/darunavir, Formula (I)/tenofovir disoproxil fumarate/efavrenz/raltegravir, Formula (I)/tenofovir disoproxil fumarate/efavrenz/rilpivirine, Formula (I)/tenofovir disoproxil fumarate/atazanavir/darunavir, Formula (I)/tenofovir disoproxil fumarate/atazanavir/raltegravir, Formula (I)/tenofovir disoproxil fumarate/atazanavir/rilpivirine, Formula (I)/tenofovir disoproxil fumarate/darunavir/raltegravir, Formula (I)/tenofovir disoproxil fumarate/darunavir/rilpivirine, Formula (I)/tenofovir disoproxil fumarate/raltegravir/rilpivirine, Formula (I)/GS-9131/emtricitabine/elvitegravir, Formula (I)/GS-9131/emtricitabine/efavrenz, Formula (I)/GS-9131/emtricitabine/atazanavir, Formula (I)/GS-9131/emtricitabine/darunavir, Formula (I)/GS-9131/emtricitabine/raltegravir, Formula (I)/GS-9131/emtricitabine/rilpivirine, Formula (I)/GS-9131/elvitegravir/efavrenz, Formula (I)/GS-9131/elvitegravir/atazanavir, Formula (I)/GS-9131/elvitegravir/darunavir, Formula (I)/GS-9131/elvitegravir/raltegravir, Formula (I)/GS-9131/elvitegravir/rilpivirine, Formula (I)/GS-9131/efavrenz/atazanavir, Formula (I)/GS-9131/efavrenz/darunavir, Formula (I)/GS-9131/efavrenz/raltegravir, Formula (I)/GS-9131/efavrenz/rilpivirine, Formula (I)/GS-9131/atazanavir/darunavir, Formula (I)/GS-9131/atazanavir/raltegravir, Formula (I)/GS-9131/atazanavir/rilpivirine, Formula (I)/GS-9131/darunavir/raltegravir, Formula (I)/GS-9131/darunavir/rilpivirine, Formula (I)/GS-9131/raltegravir/rilpivirine, Formula (I)/emtricitabine/elvitegravir/efavrenz, Formula (I)/emtricitabine/elvitegravir/atazanavir, Formula (I)/emtricitabine/elvitegravir/darunavir, Formula (I)/emtricitabine/elvitegravir/raltegravir, Formula (I)/emtricitabine/elvitegravir/rilpivirine, Formula (I)/emtricitabine/efavrenz/atazanavir, Formula (I)/emtricitabine/efavrenz/darunavir, Formula (I)/emtricitabine/efavrenz/raltegravir, Formula (I)/emtricitabine/efavrenz/rilpivirine, Formula (I)/emtricitabine/atazanavir/darunavir, Formula (I)/emtricitabine/atazanavir/raltegravir, Formula (I)/emtricitabine/atazanavir/rilpivirine, Formula (I)/emtricitabine/darunavir/raltegravir, Formula (I)/emtricitabine/darunavir/rilpivirine, Formula (I)/emtricitabine/raltegravir/rilpivirine, Formula (I)/elvitegravir/efavrenz/atazanavir, Formula (I)/elvitegravir/efavrenz/darunavir, Formula (I)/elvitegravir/efavrenz/raltegravir, Formula (I)/elvitegravir/efavrenz/rilpivirine, Formula (I)/elvitegravir/atazanavir/darunavir, Formula (I)/elvitegravir/atazanavir/raltegravir, Formula (I)/elvitegravir/atazanavir/rilpivirine, Formula (I)/elvitegravir/darunavir/raltegravir, Formula (I)/elvitegravir/darunavir/rilpivirine, Formula (I)/elvitegravir/raltegravir/rilpivirine, Formula (I)/efavrenz/atazanavir/darunavir, Formula (I)/efavrenz/atazanavir/raltegravir, Formula (I)/efavrenz/atazanavir/rilpivirine, Formula (I)/efavrenz/darunavir/raltegravir, Formula (I)/efavrenz/darunavir/rilpivirine, Formula (I)/efavrenz/raltegravir/rilpivirine, Formula (I)/atazanavir/darunavir/raltegravir, Formula (I)/atazanavir/darunavir/rilpivirine, and Formula (I)/darunavir/raltegravir/rilpivirine.

Combination Methods of Treatment

In one embodiment, the compositions of the invention that comprise a compound of formula (I) can be used alone, e.g., for inhibiting cytochrome P450 monooxygenase. In another embodiment, the compositions of the invention can be used in combination with other active therapeutic ingredients or agents. Preferably, the other active therapeutic ingredients or agents are metabolized or accessible to the oxidative metabolism by cytochrome P450 enzymes, e.g., monooxygenase enzymes such as 1A2, 2B6, 2C8, 2C19, 2C9, 2D6, 2E1, 3A4, 5, 7, etc.

It is also contemplated that the compositions of the invention that comprise a compound of formula (I) can be administered with any other active therapeutic agent or ingredient which is appreciably metabolized by cytochrome P450 monooxygenase enzymes, e.g. cytochrome P450 monooxygenase 3A, thereby reducing the amount or rate at which the other active therapeutic agent or ingredient is metabolized, whereby the pharmacokinetics of the other active therapeutic agent or ingredient is improved. Such improvements can include elevating the blood plasma levels of the other therapeutic agent or ingredient or maintaining a more therapeutically effective blood plasma level of the other therapeutic active agent or ingredient compared to blood plasma levels of the other therapeutic agent or ingredient administered without the compositions of the invention that comprise a compound of formula (I).

Co-administration of a compound of formula (I) with one or more other active therapeutic agents generally refers to simultaneous or sequential administration of a compound of formula (I) and one or more other active therapeutic agents, such that therapeutically effective amounts of the compound of formula (I) and one or more other active therapeutic agents are both present in the body of the patient.

Co-administration includes administration of unit dosages of the compounds of formula (I) before or after administration of unit dosages of one or more other active therapeutic agents, for example, administration of the compounds of formula (I) within seconds, minutes, or hours of the administration of one or more other active therapeutic agents. For example, a unit dose of a compound of formula (I) can be administered first, followed within seconds or minutes by administration of a unit dose of one or more other active therapeutic agents. Alternatively, a unit dose of one or more other therapeutic agents can be administered first, followed by administration of a unit dose of a compound of formula (I) within seconds or minutes. In some cases, it may be desirable to administer a unit dose of a compound of formula (I) first, followed, after a period of hours (e.g., 1 to 12 hours), by administration of a unit dose of one or more other active therapeutic agents. In other cases, it may be desirable to administer a unit dose of one or more other active therapeutic agents first, followed, after a period of hours (e.g., 1 to 12 hours), by administration of a unit dose of a compound of formula (I).

In yet another embodiment, the present invention provides a method for improving the pharmacokinetics of a drug which is metabolized by cytochrome P450 monooxygenase, comprising administering to a patient treated with said drug, a therapeutically effective amount of a composition of the invention that comprise a compound of formula (I) and a plurality of solid carrier particles.

In yet another embodiment, the present invention provides a method for improving the pharmacokinetics of a drug which is metabolized by cytochrome P450 monooxygenase, comprising administering to a patient treated with said drug, a therapeutically effective amount of a composition of the invention that comprise a compound of formula (I) and a plurality of silica particles that each have a surface and pores, and that have a mean particle diameter of 10 to 120 micron and a BET surface area of 40 to 400 $m^2/g$.

In yet another embodiment, the present application provides a method for improving the pharmacokinetics of a drug which is metabolized by cytochrome P450 monooxygenase, comprising administering to a patient treated with said drug, a therapeutically effective amount of a composition of the invention that comprise a compound of formula (I) and a plurality of solid carrier particles.

In yet another embodiment, the present application provides a method for improving the pharmacokinetics of a drug which is metabolized by cytochrome P450 monooxygenase, comprising administering to a patient treated with said drug, a therapeutically effective amount of a composition of the invention that comprise a compound of formula (I) and a plurality of silica particles that each have a surface and pores, and that have a mean particle diameter of 10 to 120 micron and a BET surface area of 40 to 400 $m^2/g$.

In yet another embodiment, the present application provides a method for improving the pharmacokinetics of a drug which is metabolized by cytochrome P450 monooxygenase 3A, comprising administering to a patient treated with said drug, a composition of the invention that comprise a compound of formula (I) and a plurality of solid carrier particles.

In yet another embodiment, the present application provides a method for improving the pharmacokinetics of a drug which is metabolized by cytochrome P450 monooxygenase 3A, comprising administering to a patient treated with said drug, a composition of the invention that comprise a compound of formula (I) and a plurality of silica particles that each have a surface and pores, and that have a mean particle diameter of 10 to 120 micron and a BET surface area of 40 to 400 $m^2/g$.

In yet another embodiment, the present application provides a method for increasing blood plasma levels of a drug which is metabolized by cytochrome P450 monooxygenase, comprising administering to a patient treated with said drug, a composition of the invention that comprise a compound of formula (I) and a plurality of solid carrier particles.

In yet another embodiment, the present application provides a method for increasing blood plasma levels of a drug which is metabolized by cytochrome P450 monooxygenase, comprising administering to a patient treated with said drug, a composition of the invention that comprise a compound of formula (I) and a plurality of silica particles that each have a surface and pores, and that have a mean particle diameter of 10 to 120 micron and a BET surface area of 40 to 400 $m^2/g$.

In yet another embodiment, the present application provides a method for increasing blood plasma levels of a drug which is metabolized by cytochrome P450 monooxygenase, comprising administering to a patient treated with said drug, a composition of the invention that comprise a compound of formula (I) and a plurality of solid carrier particles.

In yet another embodiment, the present application provides a method for increasing blood plasma levels of a drug which is metabolized by cytochrome P450 monooxygenase, comprising administering to a patient treated with said drug, a composition of the invention that comprise a compound of formula (I) and a plurality of silica particles that each have a surface and pores, and that have a mean particle diameter of 10 to 120 micron and a BET surface area of 40 to 400 $m^2/g$.

In yet another embodiment, the present application provides a method for increasing blood plasma levels of a drug which is metabolized by cytochrome P450 monooxygenase 3A, comprising administering to a patient treated with said drug, a composition of the invention that comprise a compound of formula (I) and a plurality of solid carrier particles.

In yet another embodiment, the present application provides a method for increasing blood plasma levels of a drug which is metabolized by cytochrome P450 monooxygenase 3A, comprising administering to a patient treated with said drug, a composition of the invention that comprise a compound of formula (I) and a plurality of silica particles that each have a surface and pores, and that have a mean particle diameter of 10 to 120 micron and a BET surface area of 40 to 400 $m^2/g$.

In yet another embodiment, the present application provides a method for inhibiting cytochrome P450 monooxygenase 3A in a patient comprising administering to a patient in need thereof an amount of a composition of the invention that comprises a compound of formula (I) and a plurality of solid carrier particles, effective to inhibit cytochrome P450 monooxygenase 3A.

In yet another embodiment, the present application provides a method for inhibiting cytochrome P450 monooxygenase 3A in a patient comprising administering to a patient in need thereof an amount of a composition of the invention that comprises a compound of formula (I) and a plurality of silica particles that each have a surface and pores, and that have a mean particle diameter of 10 to 120 micron and a BET surface area of 40 to 400 $m^2/g$, effective to inhibit cytochrome P450 monooxygenase 3A.

In yet another embodiment, the present application provides a method for treating an HIV infection comprising administering to a patient in need thereof a therapeutically effective amount of a composition of the invention that comprise a compound of formula (I) and a plurality of solid carrier particles, in combination with a therapeutically effective amount of one or more additional therapeutic agents selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, and CCR5 inhibitors.

In yet another embodiment, the present application provides a method for treating an HIV infection comprising administering to a patient in need thereof a therapeutically effective amount of a composition of the invention that comprise a compound of formula (I) and a plurality of silica particles that each have a surface and pores, and that have a mean particle diameter of 10 to 120 micron and a BET surface area of 40 to 400 $m^2/g$, in combination with a therapeutically effective amount of one or more additional therapeutic agents selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, and CCR5 inhibitors.

In yet another embodiment, the present application provides a method for treating an HIV infection comprising administering to a patient in need thereof a therapeutically effective amount of a composition of the invention that comprise a compound of formula (I) and a plurality of solid carrier particles, in combination with a therapeutically effective amount of one or more additional therapeutic agents selected from the group consisting of amprenavir, atazanavir, fosamprenavir, indinavir, lopinavir, ritonavir, nelfinavir, saquinavir, tipranavir, brecanavir, darunavir, TMC-126, TMC-114, mozenavir (DMP-450), JE-2147 (AG1776), L-756423, RO0334649, KNI-272, DPC-681, DPC-684, and GW640385X, DG17, PPL-100, DG35, AG 1859, capravirine, emivirine, delaviridine, efavirenz, nevirapine, (+) calanolide A, etravirine, GW5634, DPC-083, DPC-961, DPC-963, MIV-150, TMC-120, TMC-278 (rilpivirene), efavirenz, BILR 355 BS, VRX 840773, UK-453061, RDEA806, zidovudine, emtricitabine, didanosine, stavudine, zalcitabine, lamivudine, abacavir, amdoxovir, elvucitabine, alovudine, MIV-210, racivir (±-FTC), D-d4FC, emtricitabine, phosphazide, fozivudine tidoxil, apricitibine (AVX754), amdoxovir, KP-1461, fosalvudine tidoxil (formerly HDP 99.0003), tenofovir disoproxil fumarate, adefovir dipivoxil, curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), L-870812, L-870810, MK-0518 (raltegravir), elvitegravir, BMS-538158, GSK364735C, BMS-707035, MK-2048, and BA 011, enfuvirtide, sifuvirtide, FB006M, and TR-1144, AMD-070, an entry inhibitor, SP01A, BMS-488043, BlockAide/CR, a G6PD and NADH-oxidase inhibitor, immunitin, aplaviroc, vicriviroc, maraviroc, PRO-140, INCB15050, PF-232798 (Pfizer), CCR5mAb004, BAS-100, SPI-452, REP 9, SP-01A, TNX-355, DES6, ODN-93, ODN-112, VGV-1, PA-457 (bevirimat), Ampligen, HRG214, Cytolin, VGX-410, KD-247, AMZ 0026, CYT 99007A-221 HIV, DEBIO-025, BAY 50-4798, MDX010 (ipilimumab), PBS 119, ALG 889, and PA-1050040 (PA-040).

In yet another embodiment, the present application provides a method for treating an HIV infection comprising administering to a patient in need thereof a therapeutically effective amount of a composition of the invention that comprise a compound of formula (I) and a plurality of silica particles that each have a surface and pores, and that have a mean particle diameter of 10 to 120 micron and a BET surface area of 40 to 400 $m^2/g$, in combination with a therapeutically effective amount of one or more additional therapeutic agents selected from the group consisting of amprenavir, atazanavir, fosamprenavir, indinavir, lopinavir, ritonavir, nelfinavir, saquinavir, tipranavir, brecanavir, darunavir, TMC-126, TMC-114, mozenavir (DMP-450), JE-2147 (AG1776), L-756423, RO0334649, KNI-272, DPC-681, DPC-684, and GW640385X, DG17, PPL-100, DG35, AG 1859, capravirine, emivirine, delaviridine, efavirenz, nevirapine, (+) calanolide A, etravirine, GW5634, DPC-083, DPC-961, DPC-963, MIV-150, TMC-120, TMC-278 (rilpivirene), efavirenz, BILR 355 BS, VRX 840773, UK-453061, RDEA806, zidovudine, emtricitabine, didanosine, stavudine, zalcitabine, lamivudine, abacavir, amdoxovir, elvucitabine, alovudine, MIV-210, racivir (±-FTC), D-d4FC, emtricitabine, phosphazide, fozivudine tidoxil, apricitibine (AVX754), amdoxovir, KP-1461, fosalvudine tidoxil (formerly HDP 99.0003), tenofovir disoproxil fumarate, adefovir dipivoxil, curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), L-870812, L-870810, MK-0518 (raltegravir), elvitegravir, BMS-538158, GSK364735C, BMS-707035, MK-2048, and BA 011, enfuvirtide, sifuvirtide, FB006M, and TR-1144, AMD-070, an entry inhibitor, SP01A, BMS-488043, BlockAide/CR, a G6PD and NADH-oxidase inhibitor, immunitin, aplaviroc, vicriviroc, maraviroc, PRO-140, INCB15050, PF-232798 (Pfizer), CCR5mAb004, BAS-100, SPI-452, REP 9, SP-01A, TNX-355, DES6, ODN-93, ODN-112, VGV-1, PA-457 (bevirimat), Ampligen, HRG214, Cytolin, VGX-410, KD-247, AMZ 0026, CYT 99007A-221 HIV, DEBIO-025, BAY 50-4798, MDX010 (ipilimumab), PBS 119, ALG 889, and PA-1050040 (PA-040).

In yet another embodiment, the present application provides a method for treating an HCV infection comprising administering to a patient in need thereof a therapeutically effective amount of a composition of the invention that comprise a compound of formula (I) and a plurality of solid carrier particles, in combination with a therapeutically effective amount of one or more additional therapeutic agents selected from the group consisting of pegylated rIFN-alpha 2b, pegylated rIFN-alpha 2a, rIFN-alpha 2b, rIFN-alpha 2a, consensus IFN alpha (infergen), reaferon, intermax alpha, r-IFN-beta, infergen+actimmune, IFN-omega with DUROS, locteron, albuferon, rebif, Oral interferon alpha, IFNalpha-2b XL, AVI-005, PEG-Infergen, and pegylated IFN-beta, rebetol, copegus, viramidine (taribavirin), NM-283, valopicitabine, R1626, PSI-6130 (R1656), HCV-796, BILB 1941, XTL-2125, MK-0608, NM-107, R7128 (R4048), VCH-759, PF-868554, GSK625433, SCH-503034 (SCH-7), VX-950 (telaprevir), BILN-2065, BMS-605339, ITMN-191, MX-3253 (celgosivir), UT-231B, IDN-6556, ME 3738, LB-84451, MitoQ, benzimidazole derivatives, benzo-1,2,4-thiadiazine derivatives, phenylalanine derivatives, A-831, A-689, zadaxin, nitazoxanide (alinea), BIVN-401 (virostat), PYN-17 (altirex), KPE02003002, actilon (CPG-10101), KRN-7000, civacir, GI-5005, ANA-975, XTL-6865, ANA 971, NOV-205, tarvacin, EHC-18, NIM811, DEBIO-025, VGX-410C, EMZ-702, AVI 4065, Bavituximab, Oglufanide, and VX-497 (merimepodib).

In yet another embodiment, the present application provides a method for treating an HCV infection comprising administering to a patient in need thereof a therapeutically effective amount of a composition of the invention that comprise a compound of formula (I) and a plurality of silica particles that each have a surface and pores, and that have a mean particle diameter of 10 to 120 micron and a BET surface area of 40 to 400 $m^2/g$, in combination with a therapeutically effective amount of one or more additional therapeutic agents selected from the group consisting of pegylated rIFN-alpha 2b, pegylated rIFN-alpha 2a, rIFN-alpha 2b, rIFN-alpha 2a, consensus IFN alpha (infergen), reaferon, intermax alpha, r-IFN-beta, infergen+actimmune, IFN-omega with DUROS, locteron, albuferon, rebif, Oral interferon alpha, IFNalpha-2b XL, AVI-005, PEG-Infergen, and pegylated IFN-beta, rebetol, copegus, viramidine (taribavirin), NM-283, valopicitabine, R1626, PSI-6130 (R1656), HCV-796, BILB 1941, XTL-2125, MK-0608, NM-107, R7128 (R4048), VCH-759, PF-868554, GSK625433, SCH-503034 (SCH-7), VX-950 (telaprevir), BILN-2065, BMS-605339, ITMN-191, MX-3253 (celgosivir), UT-231B, IDN-6556, ME 3738, LB-84451, MitoQ, benzimidazole derivatives, benzo-1,2,4-thiadiazine derivatives, phenylalanine derivatives, A-831, A-689, zadaxin, nitazoxanide (alinea), BIVN-401 (virostat), PYN-17 (altirex), KPE02003002, actilon (CPG-10101), KRN-7000, civacir, GI-5005, ANA-975, XTL-6865, ANA 971, NOV-205, tarvacin, EHC-18, NIM811, DEBIO-025, VGX-410C, EMZ-702, AVI 4065, Bavituximab, Oglufanide, and VX-497 (merimepodib).

Specific Embodiments of the Invention

Specific embodiments identified herein are for illustration; they do not in any way exclude other embodiments of the invention.

In one specific embodiment the invention provides a method comprising combining the compound of formula (I):

a suitable solvent, and a plurality of solid carrier particles to provide a first mixture;

optionally mixing the first mixture;

optionally adding one or more pharmaceutically acceptable excipients (e.g. a filler, a binder and a disintegrant) to the mixture to provide a second mixture;

optionally adding another therapeutic agent to the mixture;

optionally mixing the second mixture;

optionally adding water to the second mixture to provide a wet granulate;

optionally de-agglomerating the wet granulate;

optionally drying to provide a dried material that comprises solid particles;

optionally reducing the size of the solid particles to provide a third mixture; and optionally combining the third mixture and a pharmaceutically acceptable lubricant to provide a fourth mixture.

In one specific embodiment the invention provides the first, second, third, or fourth mixture described above.

In one specific embodiment the invention provides a composition comprising, a compound of formula (I) or a pharmaceutically acceptable salt of thereof, and a plurality of silica particles that each have a surface and pores, and that have a mean particle diameter of about 10 to about 120 micron and a BET surface area of about 40 to about 400 $m^2/g$.

The invention will now be illustrated by the following non-limiting Examples.

Preparation of a Compound of Formula (Ia)

A compound of formula (Ia) or a salt thereof can be prepared by coupling an acid salt of formula X wherein M is a counterion with an amine of formula IX to form the corresponding amide of formula (Ia) as described in International Patent Application Publication Number WO 2008/103949 (for example, see page 254).

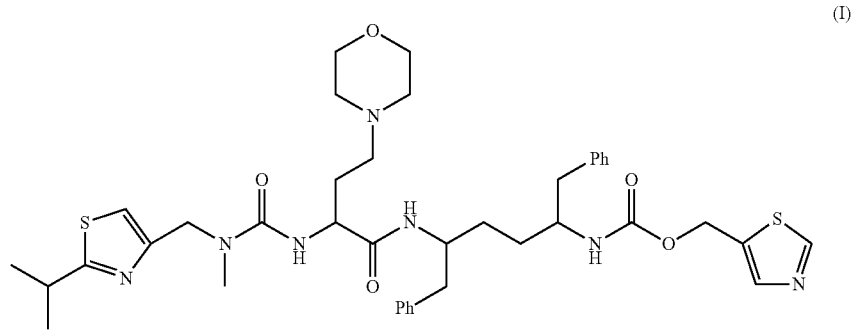 [SMILES: CC(C)c1nc(CN(C)C(=O)NC(CCN2CCOCC2)C(=O)NC(CCC(Cc2ccccc2)NC(=O)OCc2cncs2)Cc2ccccc2)cs1]

(I)

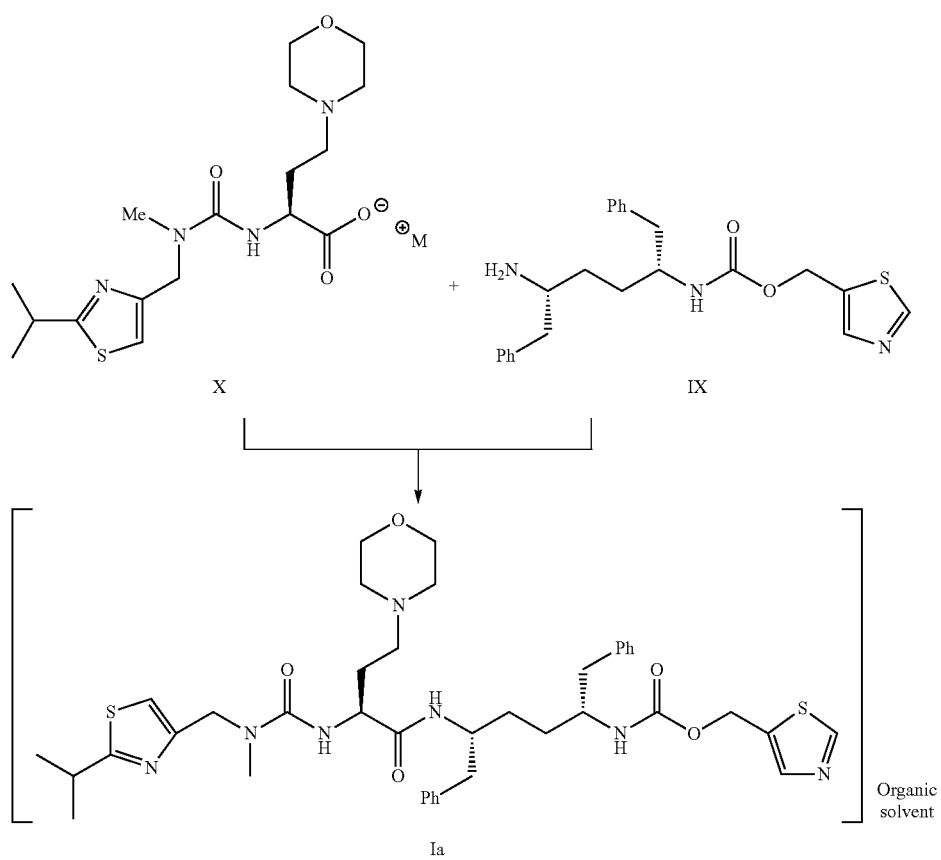

Figure 6:
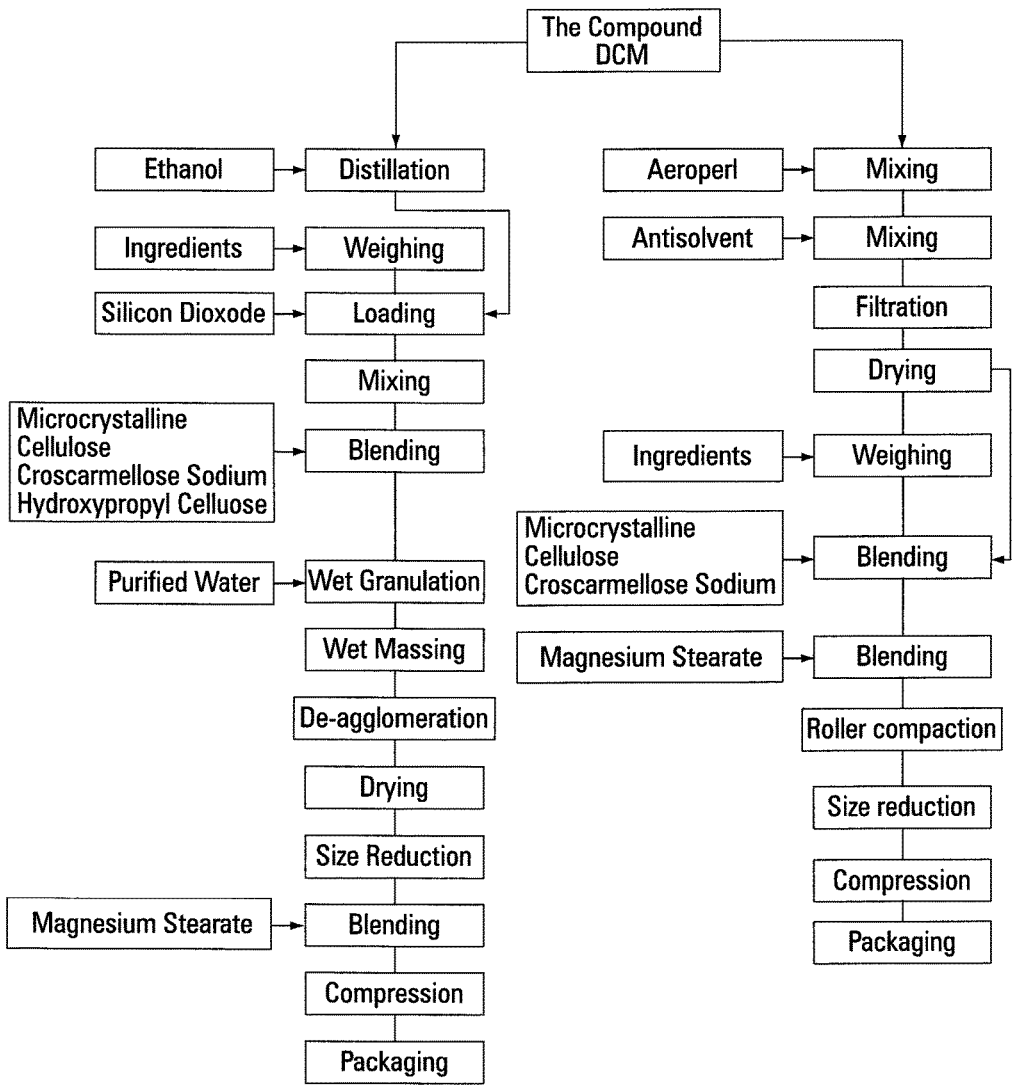
FIG. 6 Illustrates the preparation of additional a pharmaceutical formulations of the invention as well as additional processing methods of the invention.

This amide forming reaction can be carried out under standard conditions. For example, it can be carried out in a suitable organic solvent (e.g. tetrahydrofuran or dichloromethane) in the presence of a suitable coupling agent (e.g. EDC.HCl and HOBt). Other suitable amide coupling reagents and conditions are known in the field. The reaction can typically be carried out at a temperature from about −30° C. to about 20° C. The final reaction solution containing the compound of formula (Ia) in dichloromethane (DCM) can be directly utilized in the processes illustrated in FIG. 6 to provide representative compositions of the invention, or the dichloromethane solution of the compound can be combined with ethanol and the resulting mixture can be distilled to remove the dichloromethane, leaving a solution of the compound of formula (Ia) in ethanol. This ethanol solution can be combined with the silicon dioxide particles and evaporated (as illustrated in the left column of FIG. 6) to provide a composition comprising the compound of formula (Ia) loaded on silicon dioxide particles. Alternatively, the dichloromethane solution of the compound can be combined with silicon dioxide particles, an antisolvent can be added, and the resulting mixture can be filtered and dried (as illustrated in the right column of FIG. 6) to provide a composition comprising the compound of formula (Ia) loaded on silicon dioxide particles.

EXAMPLE 1

Preparation of a Representative Composition of the Invention

A solution of the compound of formula (Ia) in ethanol, prepared as described above, was used in the following preparation.

1. Weigh 374 g compound solution (0.64M) and the excipients: 195.5 g colloidal silicon dioxide, 103.7 g microcrystalline cellulose, 10.2 g hydroxypropyl cellulose, 25.5 g croscarmellose sodium, and 5.1 g magnesium stearate. Correct the weight of compound based on the solution concentration and impurities content with a concomitant reduction in the weight of microcrystalline cellulose.
2. Add colloidal silicon dioxide to a 3-L high shear granulator and spray compound solution onto the colloidal silicon dioxide over 6 to 8 minutes while mixing the powder bed at 150 rpm impeller speed.
3. Blend for an additional 2 minutes to evenly distribute the compound solution within the colloidal silicon dioxide mixture.
4. Add microcrystalline cellulose, hydroxypropyl cellulose and croscarmellose sodium to the high shear granulator/mixer and blend for 1 minute.
5. Wet granulate the blend mixture. Add purified water while mixing with the impeller at 150 rpm and the chopper at 1800 rpm to form a suitable granulation (approximately 250 to 300 g water). After water addition, wet mass with the same impeller and chopper settings for 1 minute. Add additional water and perform extra wet massing, as required, to complete granule formation.
6. Pass the wet granulation through a mill or sieve to de-agglomerate any large lumps.
7. Transfer the wet granulation to the fluid-bed dryer and dry the granules at an inlet temperature of 75° C. Dry the granules to not more than 1.0% moisture content as determined by loss on drying (LOD).
8. Pass the dried granulation through a mill with impeller rotating at 1250 rpm with a 0.032 inch round opening mill screen.
9. Add the milled, dried granulation to a suitably sized tumble blender.
10. Add magnesium stearate to the milled dried granulation and blend for 3 minutes to yield the final powder blend.
11. Compress final powder blend into tablets using a tablet press.

EXAMPLE 2

Evaluation of Water Uptake for a Representative Composition of the Invention

The water uptake for AEROPERL® 300 (fumed silica), the Compound, and a sample of AEROPERL® 300 (fumed silica) loaded with 50.0% (w/w) of the Compound was measured as described below.

The compound of formula (I) was dissolved in ethanol and this solution was poured onto a sample of fumed silica that was equal in weight to the amount of the compound of formula (I). The resulting mixture was thoroughly mixed and the solvent was evaporated to provide the compound/ AEROPERL® 300 (fumed silica) material used for the uptake study below.

The hygroscopicity of the samples was measured by dynamic vapor sorption (DVS) on a DVS Advantage-1 instrument from Surface Measurement Systems (SMS, Allentown, Pa.). In a DVS experiment the mass increase/ decrease of a sample is measured at various relative humidity (RH) levels at a constant temperature. The instrument consists of a microbalance with one pan containing the sample (typically about 5-10 mg of sample) and an empty pan as a reference, and a water vapor generator to produce the desired relative humidity level. All experiments were run at a constant temperature of 25° C. For all experiments the samples were initially dried under a continuous flow of dry nitrogen for 1 hour to establish the dry mass $m_0$. The relative humidity was then increased to 75% and the increase in mass was recorded as the samples take up water. All experiments were run until equilibrium in mass was reached at 75% R.H. (typically 10-25 hours).

Figure 2:
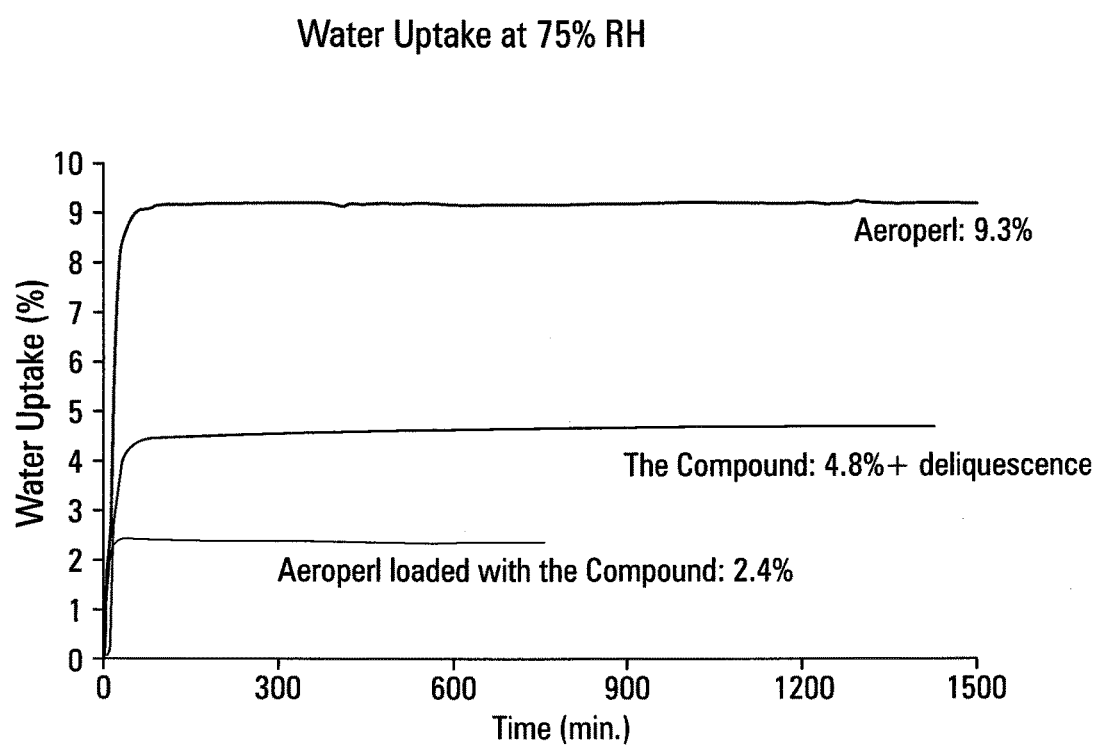
FIG. 2 Shows water uptake data from Example 2 for a representative composition of the invention.

As seen in FIG. 2 hygroscopicity of AEROPERL® 300 (fumed silica) and the Compound is significantly higher than hygroscopicity of the compound/AEROPERL® 300 (fumed silica) mixture. At 75% RH the Compound and Aeroperl adsorbed 4.8 and 9.3% (by weight) water, respectively. At the same conditions Aeroperl loaded with the Compound adsorbed only 2.4% moisture.

EXAMPLE 3

Evaluation of Compressibility for a Representative Composition of the Invention

The compressibility of a composition of the invention, a sample of AEROPERL® 300 (fumed silica) loaded with 50.0% (w/w) of the Compound, was compared to the compressibility of a similar composition lacking the Compound. The compressibility was determined using a hydraulic laboratory press (Fred Carver, Inc., Wabash, Ind., USA) with a single set of ⅜ inch round, flat-faced, beveled-edge tooling. The powder blends were compressed into compacts weighing approximately 300 mg and compressed into tablets at compression forces ranging from 500 to 2000 lb force.

Compact mass was determined using a top loading balance (Sartorius, Göttingen, Germany), compact thickness was determined using a micrometer (Absolute Digimatic, Mitutoyo, Tokyo, Japan), and compact hardness was determined using a hardness tester (VK 200, Varian, Inc., Palo Alto, Calif., USA). Tensile strength (MPa) was calculated from the mean values for ten compacts using the following equation:

$$\text{Tensile Strength (MPa)} = \frac{2 \cdot H \cdot C}{\pi \cdot T \cdot D \cdot 1000}$$

Where: H=compact hardness in kp (kilopond, 1 kp is equal to the force of 1 kg)
$C=9.807 \times 10^{-2}$ Pa·kg$^{-1}$·cm$^2$
T=compact thickness in cm
D=compact diameter in cm The compound of formula (I) was loaded onto fumed silica as described in Example 1, and the resulting material was used for the compressibility study.

Figure 3:
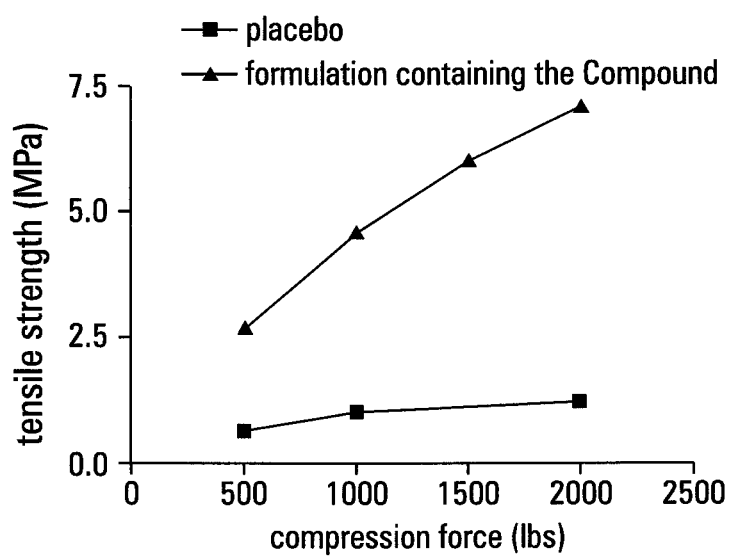
FIG. 3 Shows compressibility data from Example 3 for a representative composition of the invention.

The compressibility of the composition containing the Compound had far superior compressibility over the composition lacking the Compound (i.e., placebo) as shown in FIG. 3. The placebo composition had poor compressibility as indicated by the low tensile strength ranging from 0.6 to 1.2 MPa over the compression force range from 500 to 2000 lb. Tablets with low tensile strength lack the internal strength necessary to maintain tablet integrity during large scale tablet manufacturing and subsequent handling steps such as tablet film-coating. The composition containing the Compound had and unexpected increase in compressibility as indicated by the increase in tensile strength from 2.7 to 7.1 MPa over the compression force range from 500 to 2000 lb. This marked improvement in tensile strength allows for obtaining suitable tablet tensile strength and maintaining tablet integrity during large scale manufacturing operations.

EXAMPLE 4

Preparation of Compound I on Aeroperl

To a solution of the compound of formula (Ia) (60 g) in dichloromethane (300 mL) was charged Aeroperl (60 g) and the mixture was agitated for at least 30 minutes. After this period, heptane (1.8 L) was slowly charged over one hour. The resulting slurry was agitated for about 1 hour and the solids were isolated by filtration. The product layer was washed with heptane (500 mL). The resulting product solid was dried under vacuum at room temperature for about 24 hours. The compound of formula (I) on Aeroperl (about 50 wt %) was isolated as a white powder (112 g product, 92.5% yield).

EXAMPLE 5

Representative Formulations of the Invention

The following illustrates representative pharmaceutical dosage forms of the invention comprising compounds of formulae Ia, II, III, and IV.

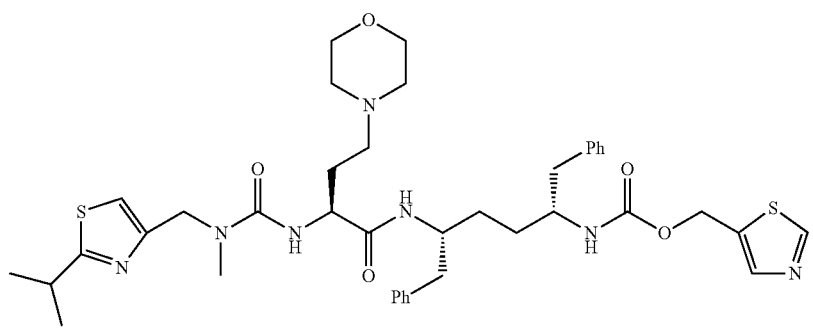 [SMILES: CC(C)c1nc(CN(C)C(=O)N[C@@H](CCN2CCOCC2)C(=O)N[C@H](CC[C@H](Cc2ccccc2)NC(=O)OCc2cncs2)Cc2ccccc2)cs1]

Ia

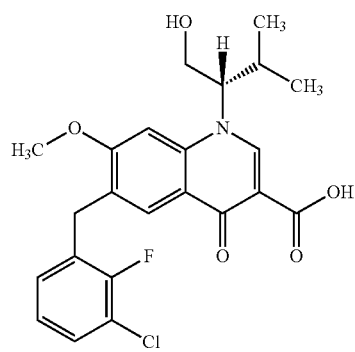 [SMILES: COc1cc2c(cc1Cc1cccc(Cl)c1F)c(=O)c(C(=O)O)cn2[C@H](CO)C(C)C]

II

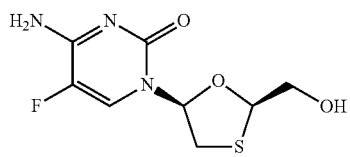 [SMILES: Nc1nc(=O)n([C@@H]2CS[C@H](CO)O2)cc1F]

III

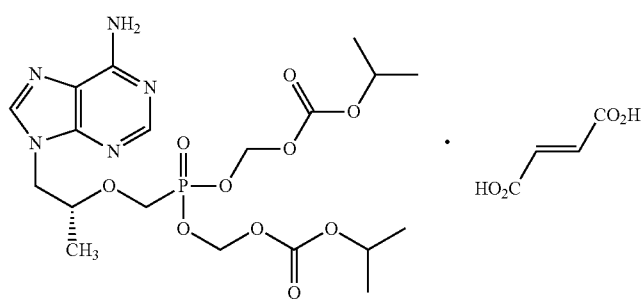 [SMILES: CC(C)OC(=O)OCOP(=O)(CO[C@H](C)Cn1cnc2c(N)ncnc21)OCOC(=O)OC(C)C ; O=C(O)/C=C/C(=O)O]

IV

| Components | Compound of Formula Ia 75 mg Formulation | | Compound of Formula Ia 100 mg Formulation | |
|---|---|---|---|---|
| | % w/w | mg/tablet | % w/w | mg/tablet |
| Compound of Formula III | 16.5 | 200.0 | 15.5 | 200.0 |
| Salt of Formula IV | 24.7 | 300.0 | 23.3 | 300.0 |
| Compound of Formula II | 12.4 | 150.0 | 11.7 | 150.0 |
| Compound of Formula Ia | 6.2 | 75.0 | 7.8 | 100.0 |
| Colloidal Silicon Dioxide | 7.1 | 86.3 | 8.9 | 115.0 |
| Lactose Monohydrate | 0.9 | 10.9 | 0.8 | 10.9 |
| Microcrystalline Cellulose | 20.9 | 253.8 | 20.9 | 269.0 |
| Hydroxypropyl Cellulose | 0.6 | 7.5 | 0.6 | 7.5 |
| Hydroxypropyl Cellulose | 0.4 | 4.5 | 0.5 | 6.0 |
| Sodium Lauryl Sulfate | 0.9 | 11.3 | 0.9 | 11.3 |
| Croscarmellose Sodium | 7.7 | 93.1 | 7.5 | 96.8 |
| Magnesium Stearate | 1.7 | 20.1 | 1.6 | 20.9 |
| Total | 100 | 1212 | 100 | 1287 |

EXAMPLE 6

Representative Formulations of the Invention

The following illustrates representative pharmaceutical dosage forms of the invention comprising compounds of formulae Ia, II, III, and IV.

| Components | Compound of Formula Ia 150 mg Formulation | |
|---|---|---|
|  | % w/w | mg/tablet |
| Compound of Formula III | 13.9 | 200.0 |
| Salt of Formula IV | 20.9 | 300.0 |
| Compound of Formula II | 10.4 | 150.0 |
| Compound of Formula Ia | 10.4 | 150.0 |
| Colloidal Silicon Dioxide | 12.0 | 172.5 |
| Lactose Monohydrate | 0.8 | 10.9 |
| Microcrystalline Cellulose | 20.8 | 299.5 |
| Hydroxypropyl Cellulose | 0.5 | 7.5 |
| Hydroxypropyl Cellulose | 0.6 | 9.0 |
| Sodium Lauryl Sulfate | 0.8 | 11.3 |
| Croscarmellose Sodium | 7.3 | 104.3 |
| Magnesium Stearate | 1.6 | 22.4 |
| Total | 100 | 1437 |

EXAMPLE 7

Representative Compositions of the Invention

In one embodiment, the invention provides a composition comprising a compound of formula (Ia) and a compound of formula (II), and a plurality of silica particles that each have a surface and pores, and that have a mean particle diameter of about 10 to about 120 micron and a BET surface area of about 40 to about 400 m$^2$/g, wherein the ratio of the compound of formula (Ia) to the compound of formula (II) is 1±0.5 by weight.

EXAMPLE 8

Representative Compositions of the Invention

In one embodiment, the invention provides a composition comprising 150 mg±10% of the compound of Formula Ia; 150 mg±10% of the compound of Formula II; 200 mg±10% of the compound of Formula III; and 300 mg±10% of the compound of Formula IV.

EXAMPLE 9

Preparation of a Representative Tablet Formulation of the Invention

The manufacturing procedure for a fixed dose combination tablet containing the compounds of Formulas Ia, II, III and IV include the following steps: 1) fluid-bed granulation and drying of the compound of Formula II, 2) high-shear granulation and fluid-bed drying of the compound of Formula Ia, 3) dry granulation of the compound of Formula III and dry granulation of the salt of Formula IV, 4) milling of the dry granulation of the compound of Formula III and milling of the dry granulation of the salt of Formula IV, 5) blending of the compound of Formula III and the salt of Formula IV, 6) blending of the compound of Formula Ia and the compound of Formula II, 7) bilayer compression with one layer consisting of the blend of the compounds of Formula Ia and Formula II and the other layer consisting of the blend of the compounds of Formula III and Formula IV to form a tablet, 8) coating of the tablet and 9) packaging of the coated tablet. The compound of formula (Ia) was loaded onto fumed silica in step 2) above using the high-shear granulation and fluid-bed drying process described in Example 1.

The in-process weight control for a bilayer tablet was superior compared to a trilayer tablet configuration. Bilayer weight control for the layer containing the compounds of Formula Ia and Formula II was between 100.2% and 100.8% of the mean target layer weight. Mean weights for the total tablet was between 99.5% and 100.7% of the mean target tablet weight. The relative standard deviation (RSD) value for the layer containing the compounds of Formula Ia and Formula II was between 1.4% and 2.2%, while the RSD for the total tablet was between 0.7% and 1.2%. These low RSD values indicate very low weight variability during the bilayer tablet compression process. The friability at the start and end of the compression process was 0.0%. No chipped, capped, or broken tablets were observed during bilayer compression.

EXAMPLE 10

Preparation of a Representative Composition of the Invention

A representative composition of the invention having silicon dioxide as the solid carrier was prepared as described below.
1. Weigh 7.7 g compound solution (in ethanol) and the excipients: 3.83 g silicon dioxide, 2.03 g microcrystalline cellulose, 0.2 g hydroxypropyl cellulose, 0.5 g croscarmellose sodium, and 0.1 g magnesium stearate. Correct the weight of compound based on the solution concentration and impurities content with a concomitant reduction in the weight of microcrystalline cellulose.
2. Add silicon dioxide (syloid 244) to a mortar and pour compound solution onto the silicon dioxide over 1-2 minutes while mixing the powder with pestle.
3. Mix for an additional 2 minutes to evenly distribute the compound solution within the silicon dioxide mixture.
4. Add microcrystalline cellulose, hydroxypropyl cellulose and croscarmellose sodium to the mortar and mix for 1 minute.
5. Wet granulate the blend mixture. Add purified water while mixing with pestle to form a suitable granulation (approximately 7.5 g water).
6. Pass the wet granulation through a sieve to de-agglomerate any large lumps.
7. Transfer the wet granulation to a shelf drier and dry the granules at 50° C. Dry the granules to not more than 1.0% moisture content as determined by loss on drying (LOD).
8. Pass the dried granulation through a sieve.
9. Add the milled, dried granulation to a suitably sized tumble blender.
10. Add magnesium stearate to the milled dried granulation and blend for 1 minute to yield the final powder blend.
11. Compress final powder blend into tablets using a tablet press.

Additional representative compositions of the invention were also prepared using a procedure similar to the one described above, except replacing the silicon dioxide used therein with talc, Aerosil 200, or Aerosl 200 VV.

EXAMPLE 11

Preparation of a Representative Composition of the Invention

Figure 4:
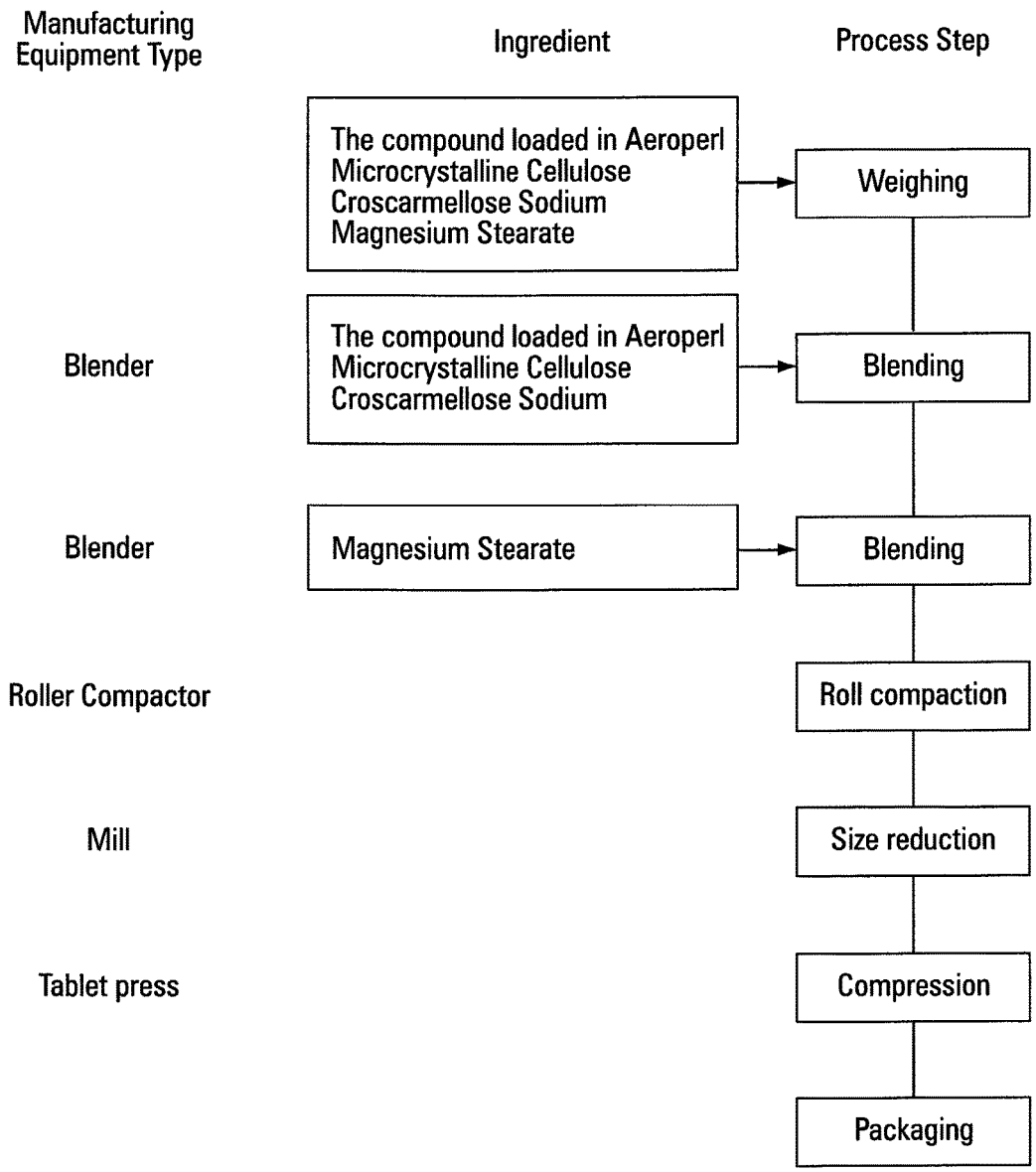
FIG. 4 Illustrates the preparation of a pharmaceutical formulation of the invention as well as processing methods of the invention.

A representative composition of the invention was prepared as described below and as illustrated in FIG. 4.

1. Weigh 74.4 g compound I loaded in Aeroperl (prepared as described in Example 4) and the excipients: 20.1 g microcrystalline cellulose, 5.02 g croscarmellose sodium, and 0.5 g magnesium stearate. Correct the weight of compound based on the % loading of compound onto silica and impurities content with a concomitant reduction in the weight of microcrystalline cellulose.
2. Add compound I in Aeroperl, microcrystalline cellulose and croscarmellose sodium to a blender. Blend for 5 minutes.
3. Add magnesium stearate and blend for 3 minutes.
4. Dry granulate blend using roller compactor. Use following parameters: gap=1.5 mm, force of 3.0 kN and screen size 0.8 mm
5. Pass the granulation through a mill or sieve to break larger granules.
6. Compress final powder blend into tablets using a tablet press.

EXAMPLE 12

Preparation of a Representative Composition of the Invention

Figure 5:
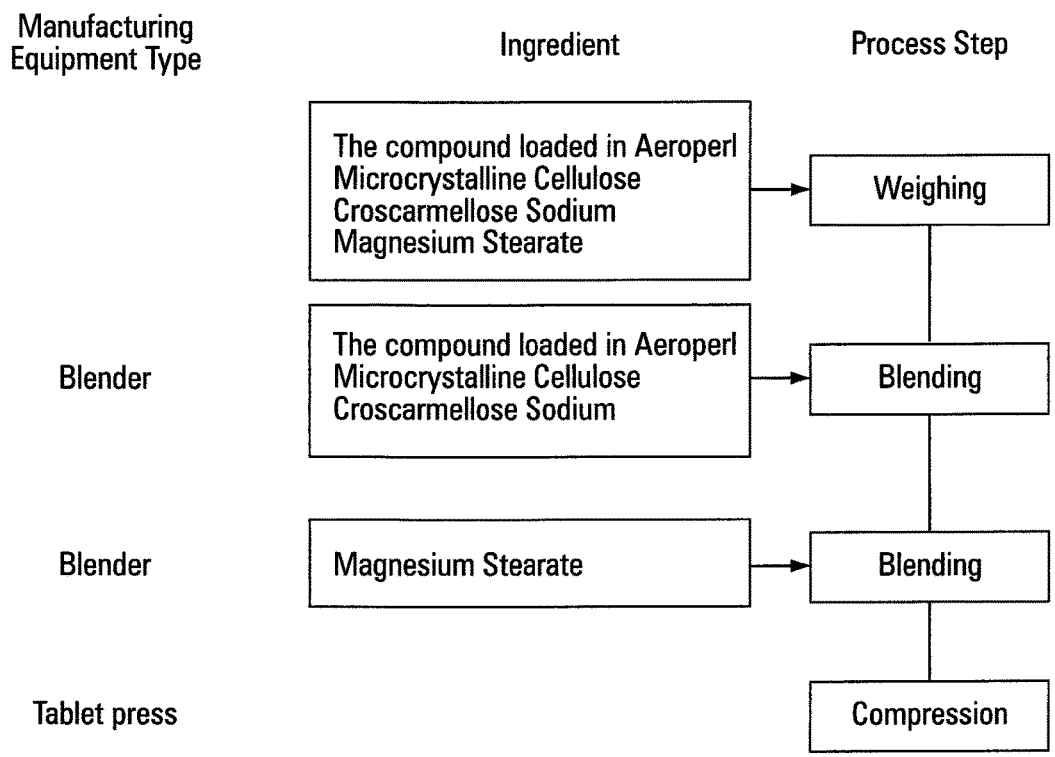
FIG. 5 Illustrates the preparation of a pharmaceutical formulation of the invention as well as processing methods of the invention.

A representative composition of the invention can be prepared as described below and as illustrated in FIG. 5. Weigh 40.9 g compound I loaded in Aeroperl (prepared as described in Example 4) and the excipients: 15.8 g microcrystalline cellulose, 3.0 g croscarmellose sodium, and 0.3 g magnesium stearate. Correct the weight of compound based on the % loading of compound onto silica and impurities content with a concomitant reduction in the weight of microcrystalline cellulose.
1. Add compound I in Aeroperl, microcrystalline cellulose and croscarmellose sodium to a blender. Blend for 5 minutes.
2. Add magnesium stearate and blend for 3 minutes.
3. Compress final powder blend into tablets using a tablet press.

EXAMPLE 13

Representative Formulations of the Invention

The following illustrate representative pharmaceutical dosage forms, containing a compound of formula I ('Compound X'), for therapeutic or prophylactic use in humans.

| Tablet 1 | mg/tablet |
|---|---|
| Compound X | 10.0 |
| Silicon Dioxide (AEROPERL ® 300 (fumed silica) | 115.0 |
| Microcrystalline cellulose (Avicel PH101) | 151.0 |
| Hydroxypropyl Cellulose (Klucel LF) | 6.0 |
| Croscarmellose sodium (Ac-Di-Sol) | 15.0 |
| Magnesium stearate (Hyqual) | 3.0 |
| | 300.0 |

| Tablet 2 | mg/tablet |
|---|---|
| Compound X | 25.0 |
| Silicon Dioxide AEROPERL ® 300 (fumed silica) | 115.0 |
| Microcrystalline cellulose (Avicel PH101) | 136.0 |
| Hydroxypropyl Cellulose (Klucel LF) | 6.0 |
| Croscarmellose sodium (Ac-Di-Sol) | 15.0 |
| Magnesium stearate (Hyqual) | 3.0 |
| | 300.0 |

| Tablet 3 | mg/tablet |
|---|---|
| Compound X | 100.0 |
| Silicon Dioxide AEROPERL ® 300 (fumed silica) | 115 |
| Microcrystalline cellulose (Avicel PH101) | 61.0 |
| Hydroxypropyl Cellulose (Klucel LF) | 6.0 |
| Croscarmellose sodium (Ac-Di-Sol) | 15.0 |
| Magnesium stearate (Hyqual) | 3.0 |
| | 300.0 |

| Tablet 4 | mg/tablet |
|---|---|
| Compound X | 150.0 |
| Silicon Dioxide (e.g. Syloid 244) | 172.5 |
| Microcrystalline cellulose (Avicel PH101) | 91.5 |
| Hydroxypropyl Cellulose (Klucel LF) | 9.0 |
| Croscarmellose sodium (Ac-Di-Sol) | 22.5 |
| Magnesium stearate (Hyqual) | 4.5 |
| | 450.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A composition comprising a plurality of hydrophilic fumed silicon dioxide particles and a compound of formula (I):

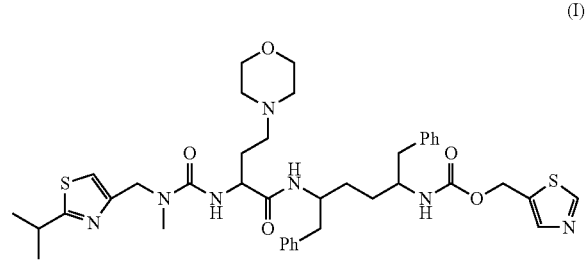 [SMILES: CC(C)c1nc(CN(C)C(=O)NC(CCN2CCOCC2)C(=O)NC(CCC(Cc2ccccc2)NC(=O)OCc2cncs2)Cc2ccccc2)cs1]

wherein the compound of formula (I) is in the pores or on the surface of the silicon dioxide particles.

2. The composition of claim 1 wherein the silicon dioxide particles have a mean grain diameter of 20-40 micron.

3. The composition of claim 1 wherein the silicon dioxide particles have a BET surface area of at least 150 $m^2/g$.

4. The composition of claim 1 wherein the compound of formula (I) has an enriched concentration of 99±1% of the stereoisomer of formula (Ia):

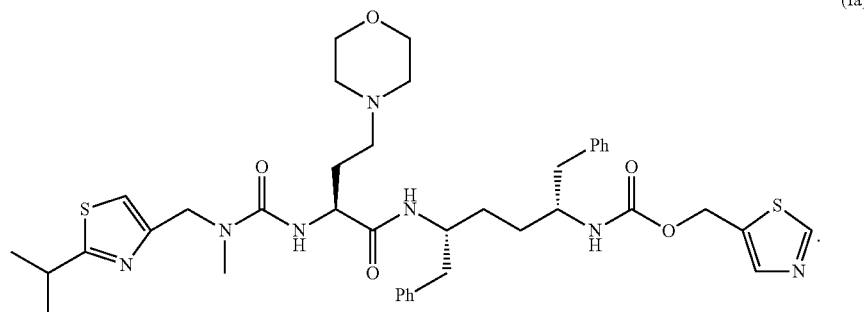

(Ia)

5. A method of preparing the composition of claim 1 comprising combining the compound of formula (I):

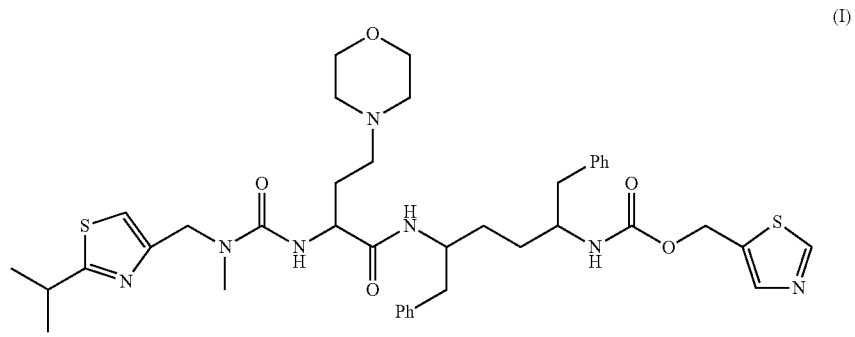 [SMILES: CC(C)c1nc(CN(C)C(=O)NC(CCN2CCOCC2)C(=O)NC(CCC(Cc2ccccc2)NC(=O)OCc2cncs2)Cc2ccccc2)cs1]

(I)

a suitable solvent, and a plurality of hydrophilic fumed silicon dioxide particles to provide a mixture, wherein the compound of formula (I) is in the pores or on the surface of the silicon dioxide particles.

6. The method of claim 5 wherein the silicon dioxide particles have a mean grain diameter of 20-40 micron.

7. The method of claim 5 wherein the silicon dioxide particles have a BET surface area of at least 150 m²/g.

8. The method of claim 5 wherein the solvent is a ($C_1$-$C_6$) alcohol.

9. The method of claim 5 wherein the solvent comprises ethanol.

10. A pharmaceutical composition comprising a plurality of hydrophilic fumed silicon dioxide particles; a compound of formula (I):

tenofovir disoproxil fumarate; emtricitabine; and elvitegravir; wherein the compound of formula (I) is in the pores or on the surface of the silicon dioxide particles.

11. The pharmaceutical composition of claim 10 wherein the silicon dioxide particles have a mean grain diameter of 20-40 micron.

12. The pharmaceutical composition of claim 10 wherein the silicon dioxide particles have a BET surface area of at least 150 m²/g.

13. The pharmaceutical composition of claim 10 wherein the compound of formula (I) has an enriched concentration of 99±1% of the stereoisomer of formula (Ia):

(I)

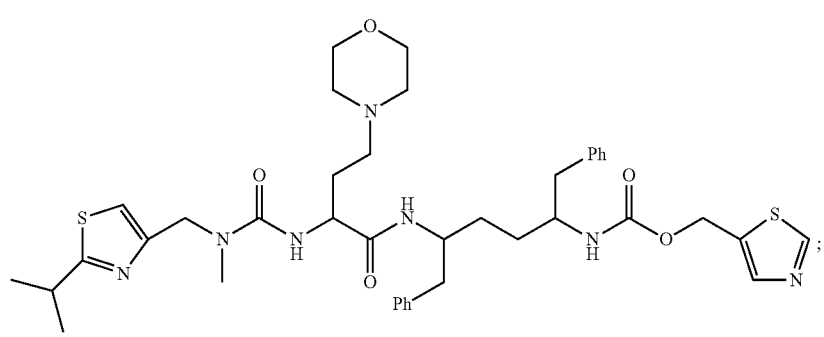

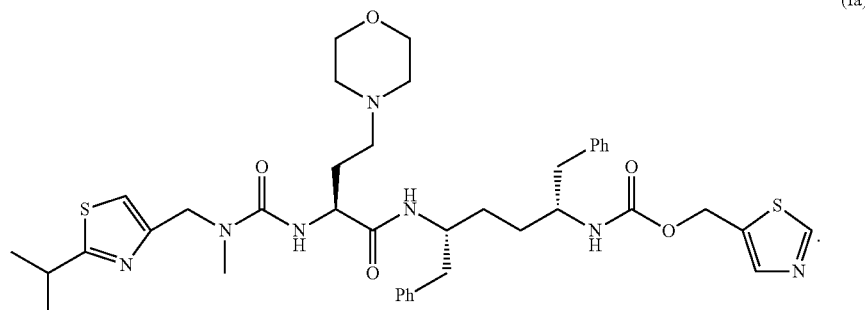

(Ia)

14. The composition of claim 4, further comprising at least one additional therapeutic agent selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, non-nucleoside inhibitors of HCV, CCR5 inhibitors, and combinations thereof, and a pharmaceutically acceptable excipient.

15. The composition of claim 14, wherein the additional therapeutic agent is darunavir.

16. The composition of claim 14, wherein the additional therapeutic agent is atazanavir.

17. The composition of claim 4, comprising 150 mg±10% of the compound of formula (Ia).

18. The composition of claim 1, wherein the silicon dioxide particles have a mean particle diameter of about 10 to about 120 micron and a BET surface area of about 40 to about 400 $m^2/g$.

19. The composition of claim 1, wherein the weight of the compound of formula (I) divided by the weight of the silicon dioxide particles in the composition is 1.0±0.5.

20. The composition of claim 1, wherein the hygroscopicity of the silicon dioxide particles and the compound of formula (I) taken separately is higher than the hygroscopicity of the compound of formula (I) and silicon dioxide particles taken together.

21. The method of claim 5, wherein the silicon dioxide particles have a mean particle diameter of about 10 to about 120 micron and a BET surface area of about 40 to about 400 $m^2/g$.

22. The method of claim 5, wherein the weight of the compound of formula (I) divided by the weight of the silicon dioxide particles in the mixture is 1.0±0.5.

23. The method of claim 5, wherein the hygroscopicity of the silicon dioxide particles and the compound of formula (I) taken separately is higher than the hygroscopicity of the compound of formula (I) and silicon dioxide particles taken together.

24. The pharmaceutical composition of claim 10, wherein the silicon dioxide particles have a mean particle diameter of about 10 to about 120 micron and a BET surface area of about 40 to about 400 $m^2/g$.

25. The pharmaceutical composition of claim 10, wherein the weight of the compound of formula (I) divided by the weight of the silicon dioxide particles in the composition is 1.0±0.5.

26. The pharmaceutical composition of claim 10, wherein the hygroscopicity of the silicon dioxide particles and the compound of formula (I) taken separately is higher than the hygroscopicity of the compound of formula (I) and silicon dioxide particles taken together.

* * * * *

UNITED STATES PATENT AND TRADEMARK OFFICE
CERTIFICATE OF CORRECTION

PATENT NO. : 10,039,718 B2
APPLICATION NO. : 12/434513
DATED : August 7, 2018
INVENTOR(S) : Koziara et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1254 days.

Signed and Sealed this
Fourteenth Day of July, 2020

Andrei Iancu
*Director of the United States Patent and Trademark Office*